United States Patent
Sill et al.

(10) Patent No.: US 10,143,689 B2
(45) Date of Patent: Dec. 4, 2018

(54) SN-38 LOADED IRON CROSSLINKED MICELLE AND METHODS THEREOF

(71) Applicant: Intezyne Technologies, Inc., Tampa, FL (US)

(72) Inventors: Kevin N. Sill, Tampa, FL (US); Adam Carie, Tampa, FL (US)

(73) Assignee: Interzyne Technologies, Inc., Tampa, FL (US)

(*) Notice: Subject to any disclaimer, the term of this patent is extended or adjusted under 35 U.S.C. 154(b) by 0 days.

(21) Appl. No.: 15/892,216

(22) Filed: Feb. 8, 2018

(65) Prior Publication Data

US 2018/0228796 A1    Aug. 16, 2018

Related U.S. Application Data

(66) Substitute for application No. 62/581,089, filed on Nov. 3, 2017.

(60) Provisional application No. 62/456,396, filed on Feb. 8, 2017.

(51) Int. Cl.

| | | |
|---|---|---|
| A61K 31/4745 | (2006.01) | |
| A61K 47/02 | (2006.01) | |
| A61K 47/26 | (2006.01) | |
| A61K 47/34 | (2017.01) | |
| A61P 35/00 | (2006.01) | |
| A61K 9/107 | (2006.01) | |

(52) U.S. Cl.
CPC ........ *A61K 31/4745* (2013.01); *A61K 9/1075* (2013.01); *A61K 47/02* (2013.01); *A61K 47/26* (2013.01); *A61K 47/34* (2013.01); *A61P 35/00* (2018.01)

(58) Field of Classification Search
CPC .. A61K 31/4745; A61K 9/1075; A61K 47/02; A61K 47/26; A61K 47/34
USPC ........................................................ 514/283
See application file for complete search history.

(56) References Cited

U.S. PATENT DOCUMENTS

| | | | |
|---|---|---|---|
| 7,601,796 B2 | 10/2009 | Breitenkamp et al. | |
| 7,638,558 B2 | 12/2009 | Breitenkamp et al. | |
| 7,799,339 B2 | 9/2010 | Sill et al. | |
| 8,263,663 B2 | 9/2012 | Sill et al. | |
| 8,263,665 B2 | 9/2012 | Sill et al. | |
| 8,299,128 B2 | 10/2012 | Sill et al. | |
| 8,426,477 B1 | 4/2013 | Breitenkamp et al. | |
| 8,609,146 B2 | 12/2013 | Sill et al. | |
| 8,779,008 B2 | 7/2014 | Breitenkamp et al. | |
| 8,980,326 B2 | 3/2015 | Sill et al. | |
| 9,078,930 B2 | 7/2015 | Sill et al. | |
| 9,499,665 B2 | 11/2016 | Sill et al. | |
| 9,944,752 B2 | 4/2018 | Sill et al. | |
| 9,944,754 B2 | 4/2018 | Sill et al. | |
| 2008/0274173 A1 | 11/2008 | Sill et al. | |
| 2009/0036611 A1 | 2/2009 | Wilker et al. | |
| 2010/0278927 A1 | 11/2010 | Mirosevich et al. | |
| 2010/0278932 A1 | 11/2010 | Sill et al. | |
| 2010/0305148 A1 | 12/2010 | Soon-Shiong et al. | |
| 2010/0324259 A1 | 12/2010 | Sill et al. | |
| 2013/0280306 A1 | 10/2013 | Sill et al. | |
| 2013/0288991 A1 | 10/2013 | Sill et al. | |
| 2013/0296531 A1 | 11/2013 | Sill et al. | |
| 2014/0113879 A1 | 4/2014 | Carie et al. | |
| 2014/0114051 A1 | 4/2014 | Semple | |
| 2014/0127271 A1 | 5/2014 | Sill et al. | |
| 2015/0232616 A1 | 8/2015 | Sill et al. | |
| 2015/0368401 A1 | 12/2015 | Sill et al. | |
| 2016/0264732 A1 | 9/2016 | Sill et al. | |

FOREIGN PATENT DOCUMENTS

| | | |
|---|---|---|
| WO | 2006107903 A2 | 10/2006 |
| WO | 2008134731 A1 | 11/2008 |
| WO | 2010129581 A1 | 11/2010 |
| WO | 2013154774 A1 | 10/2013 |

OTHER PUBLICATIONS

International Search Report and Written Opinion for PCT/US2018/017454, 7 pages (dated Apr. 26, 2018).
Cho et al., Synthesis and characterization of di- and triblock copolymers of poly(ethylene oxide) and poly(DL-valine-co-DL-leucine), Polymer, vol. 44, Jun. 2003, 5497-5500.
Derycke et al, "Transferrin-conjugated liposome targeting of photosensitizer AlPcS4 to rat bladder carcinoma cells," Journal of the National Cancer Institute, vol. 96, No. 21, Nov. 3, 2004 (pp. 1620-1630).
Gabizon et al., "Tumor cell targeting of liposome-entrapped drugs with phospholipid-anchored folic acid-PEG conjugates," Advanced Drug Delivery Reviews, vol. 56, No. 8, Apr. 2004 (pp. 1177-1192).
Jones et al., "Antibodies for targeted gene therapy: extracellular gene targeting and intracellular expression," Advanced Drug Delivery Reviews, vol. 31, No. 1-2, Apr. 1998 (pp. 153-170).
Jule et al., "Lactose-Installed Poly(ethylene glycol)-Poly(d,I-lactide) Block Copolymer Micelles Exhibit Fast-Rate Binding and High Affinity toward a Protein Bed Simulating a Cell Surface. A Surface Plasmon Resonance Study," Bioconjugate Chemistry, vol. 14, No. 1, 2003 (pp. 177-186).
Kumar et al., "UPLC and LC-MS Studies on Degradation Behavior of Irinotecan Hydrochloride and Development of a Validated Stability-Indicating Ultra-Performance Liquid Chromatographic Method for Determination of Irinotecan Hydrochloride and its Impurities in Pharmaceutical Dosage Forms," Journal of Chromatographic Science. Jun. 1, 2012 vol. 50, p. 810-819.
Kurschus et al., "Killing of target cells by redirected granzyme B in the absence of perforin," FEBS Letters, vol. 562, No. 1-3, Mar. 2004 (pp. 87-92).
Lu et. al., "Stability of Self-Assembled Polymeric Micelles in Serum," Macromolecules, vol. 44, No. 15, 2011 (pp. 6002-6008).
Nasongkla et al., "cRGD-functionalized polymer micelles for targeted doxorubicin delivery," Angewandte Chemie International Edition, vol. 43, No. 46, Nov. 2004 (pp. 6323-6327).

(Continued)

*Primary Examiner* — Yevgeny Valenrod
(74) *Attorney, Agent, or Firm* — Andrea L. C. Reid; Dechert LLP

(57) ABSTRACT

The present invention provides SN-38 compositions for treating cancer.

16 Claims, 12 Drawing Sheets

(56) References Cited

OTHER PUBLICATIONS

Pan et al., "Folic acid-conjugated nanostructured materials designed for cancer cell targeting," Chemical Communications, vol. 19, 2003 (pp. 2400-2401).

Paolillo et al., "Nuclear magnetic resonance and optical spectroscopic studies of copolymers of polypeptides. II. Random copoly(benzyl-L-glutamate: Benzyl-L-aspartate) and (benzyl-D-glutamate: benzyl-L-aspartate)," Biopolymers, vol. 11, No. 10, Oct. 1972 (pp. 2043-2052).

Reynolds et al., "Insertion of an RGD motif into the HI loop of adenovirus fiber protein alters the distribution of ransgene expression of the systematically administered vector," Gene Therapy, vol. 6, 1999 (pp. 1336-1339).

Rosthauser et al., "Crosslinking of hydroxamic acid copolymers through iron chelation," Macromolecules, vol. 14, No. 3, 1981 (pp. 538-543).

Sakai et al., "The Structure of Copolymers of L-Proline with γ-Benzyl-L-glutamate in Organic Solvents," Bulletin of the Chemical Societ of Japan, vol. 42, No. 5, No Month Listed 1969 (pp. 1332-1336).

Savic et. al., "Assessment of the Integrity of Poly(caprolactone)-b-poly(ethylene oxide) Micelles under Biological Conditions: A Fluorogenic-Based Approach," Langmuir, vol. 22, No. 8, 2006 (pp. 3570-3578).

Stubenrauch et al., "Conjugation of an antibody Fv fragment to a virus coat protein: cell-specific targeting of recombinant polyomavirus-like particles," Biochemical Journal, vol. 356, No. 3, Jun. 2001 (pp. 867-873).

Aideh, K. et al., Synthesis of iron-crosslinked chitosan succinate and iron-crosslinked hydroxamated chitosan succinate and their in vitro evaluation as potential matrix materials for oral theophyllne sustained-release beads, European Journal of Pharmaceutical Sciences, 13:159-168 (2001).

Aisen, P. et al., Stiochiometric and site characteristics of the binding of iron to human transferrin, J. Bioi. Chem., 253 (6): 1930-1937 (1978).

Ajith, S. and Rakshit, A.K., Effect of NaCl on a Nonionic Surfactant Microemulsion System, Langmuir, 11:1122-1126 (1995).

Andres, G.O. and Rossi, R.H., Mechanism of phthalate ester hydrolysis in water and in cyclodextrin mediated reactions, ARKIVOA, 127-138 (2003).

Crowe, L.M. et al., Is trehalose special for preserving dry biomaterials?, Biophysical Journal, 71:2087-2093 (1996).

Eby, G.A., Zinc ion availability—the determinant of efficacy in zinc lozenge treatment of common colds, Journal of Antimicrobial Chemotherapy, 40:483-493 (1997).

Extended European Search Report for EP13001333.7, 5 pages (dated Oct. 4, 2013).

Genbank Entry, AAN17825: for Human Serum Albumin, 1 (2013).

Giroux, E.L. and Henkin, R.I., Competition for Zinc Among Serum Albumin and Amino Acids, Biochimica et Biophysica Acta, 273:64-72 (1972).

Honzl, J. and Rudinger, J., Synthetic studies in the oxytocin field. II. The synthesis of some dertivatives of I-cysteinyl-I-tyrosylglycine, I-cysteinyl-I-leucine and I-cysteinyl-I-isoleucine, Collection of Czechoslovakian Chemical Communications, 1190-1198 (1955).

Hoshi, A. et al., Antitumor Activity of Berberrubine Derivatives, Gann, 67(2):321-325 (1976).

Hutcheson, R.M. et al., Voltammetric studies of zn and fe complexes of edta: evidence for the push mechanism, Biometals, 18: 43-51 (2005).

International Search Report and Written Opinion for PCT/US2013/032409, 7 pages (dated Jun. 10, 2013).

Izutsu, K., Stabilization of Therapeutic Proteins by Chemical and Physical Methods, Methods in Molecular Biology, 308:287-292 (2005).

Janssen, S. et al., Screening a combinatorial peptide library to develop a human glandular kallikrein 2-activated prodrug as targeted therapy for prostate cancer, Molecular Cancer Therapy, 3(11):1439-1450 (2004).

Jolivet, J. et al., Iron Oxide Chemistry. From Molecular Clusters to Extended Solid Networks, Chemical Communications, 481-487 (2004).

Jurado, R.L., Iron, Infections, and Anemia of Inflammation, Clinical Infectious Diseases, 25:888-895 (1997).

Kakizawa, Y. et al., Environment-Sensitive Stabilization of Core-Shell Structures Polyion Complex Michelle by Reversible Cross-Linking of the Core through Disulfide Bond, Journal of Americal Chemical Society, 121:11247-11248 (1999).

Kozlowski, H. et al., The Influence of Aspartic or Glutmaic Acid Residues in Tetrapeptides on the Formation of Complexes with Nickel(II) and Zinc(II), Polyhedron, 14(2):211-218 (1995).

Li, J. and Sha, Y., A convenient synthesis of amino acid methyl esters, Molecules, 13: 1111-1119 (2008).

Li, Y. et al., pH-Responsive Shell Cross-Linked Nanoparticles with Hydrolytically Labile Cross-Links, Macromolecules, xx(x):1-3 (2008).

Li, Y. et al., Well-Defined, Reversible Boronate Crosslinked Nanocarriers for Targeted Drug Delivery in Response to Acidic pH Values and cis-Diols, Agnewandte Chemie International Edition, 51:1-7 (2012).

Liu, S. et al., Synthesis of Shell Cross-Linked Micelles with pH-Responsive Cores Using ABC Triblock Copolymers, Macromolecules, 35:6121-6131 (2002).

Lokitz, B.S. et al., Aqueous Raft Synthesis of Micelle-Forming Amphiphilic Block Copolymers Containing N-Acryloylvaline. Dual Mode, Temperature/pH Responsiveness, and "Locking" of Micelle Structure through Interpolyelectrolyte Complexation, Macromolecules, 40(18):6473-6480 (2007).

Lu, J. et al., Stability of Self-Assembled Polymeric Micelles in Serum, Macromolecules, 44:6002-6008 (2011).

March, J., Advanced Organic Chemistry, Reactions, Mechanisms, and Structure, 4:421-424 (1992).

Miller, M.J., Syntheses and Therapeutic Potential of Hydroxamic Acid Based Siderophores and Analogues, Chemical Review, 89(7):1563-1579 (1989).

Miyata, K. et al., Block Catiomer Polyplexes with Regulated Densities of Charge and Disulfide Cross-Linking Directed to Enhance Gene Expression, Journal of American Chemical Society, 126:2355-2361 (2004).

Neilands, J.B., Hydroxamic Acids in Nature, Science, 156(3781):1443-1447 (1967).

Nishiyama, N. et al., Preparation and Characterization of Self-Assembled Polymer-Metal Complex Michelle from cis-Dichlorodiammineplatinum (II) and Poly(ethylene glycol)-Poly($\alpha$,($\beta$-aspartic acid) Block Copolymer in an Aqueous Medium, Langmuir, 15(2):377-383 (1999).

Oikawa, A. et al., Chemical analysis of acetylated bovine growth hormone, a growth hormone inhibitor, Biochemistry Journal, 104:947-952 (1967).

Owen, W.F. et al., The Urea Reduction Ratio and Serum Albumin Concentration as Predictors of Mortality in Patients Undergoing Hemodialysis, The New England Journal of Medicine, 329(14):1001-1006 (1993).

Popuri, S.R. et al., Adsorptive removal of copper and nickel ions from water using chitsan coated pvc beads, Bioresource Tech., 100: 194-199 (2009).

Read, E.S. and Armes, S.P., Recent advances in shell cross-linked micelles, Chemical Communications, 3021-3035 (2007).

Rosthauser, J.W. and Winston, A., Cross-Linking of Hydroxamic Acid Copolymers through Iron Chelation, Macromolecules, 14:538-343 (1981).

Savic, R. et al., Assessment of the Integrity of Poly(caprolactone)-b-poly(ethylene oxide) Micelles under Biological Conditions: A Fluorogenic-Based Approach, Langmuir, 22(8):3570-8 (2006).

Schoenbach, E.B. et al., Observations on the Effects of the Folic Acid Antagonists, Aminopterin and Amethopterin, in Patients with Advanced Neoplasms, Cancer, 5(6):1201-1220 (1952).

"The University of Wisconsin-Madison's chemical of the week for chelating agents,<http://scifun.chem.wisc.edu/chemweek!chelates/chelates.html> Available Online (Jul. 1998)."

(56) References Cited

OTHER PUBLICATIONS

Weisberg, E. et al., Smac mimetics: implications for enhancement of targeted therapies in leukemia, Leukemia, 24:2100-2109 (2010).
Winston, A. and Kirchner, D., Hydroxamic acid polymers: Effect of structure on the selective chelation of iron in water, Macromolecules, 11(3):597-603 (1978).

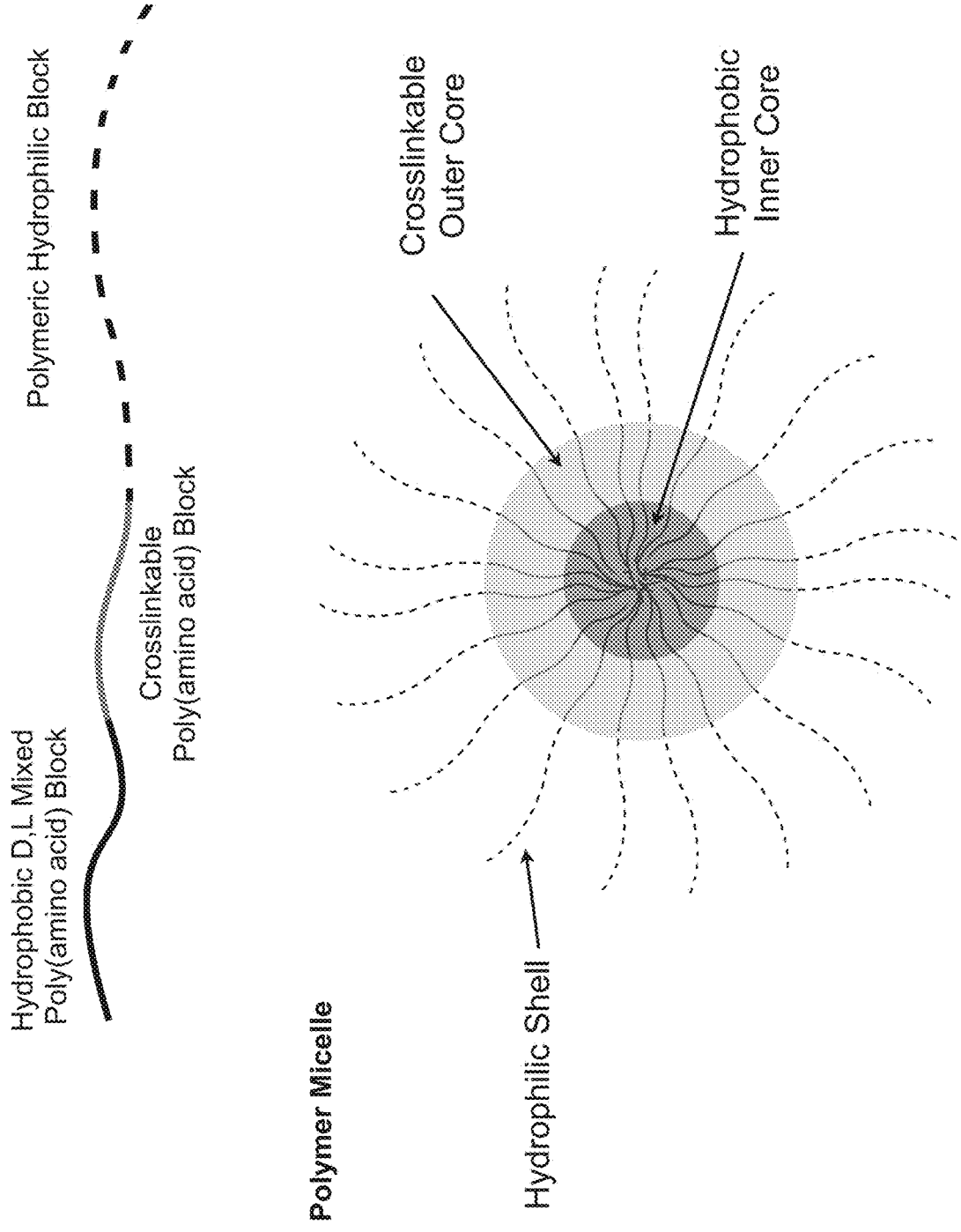

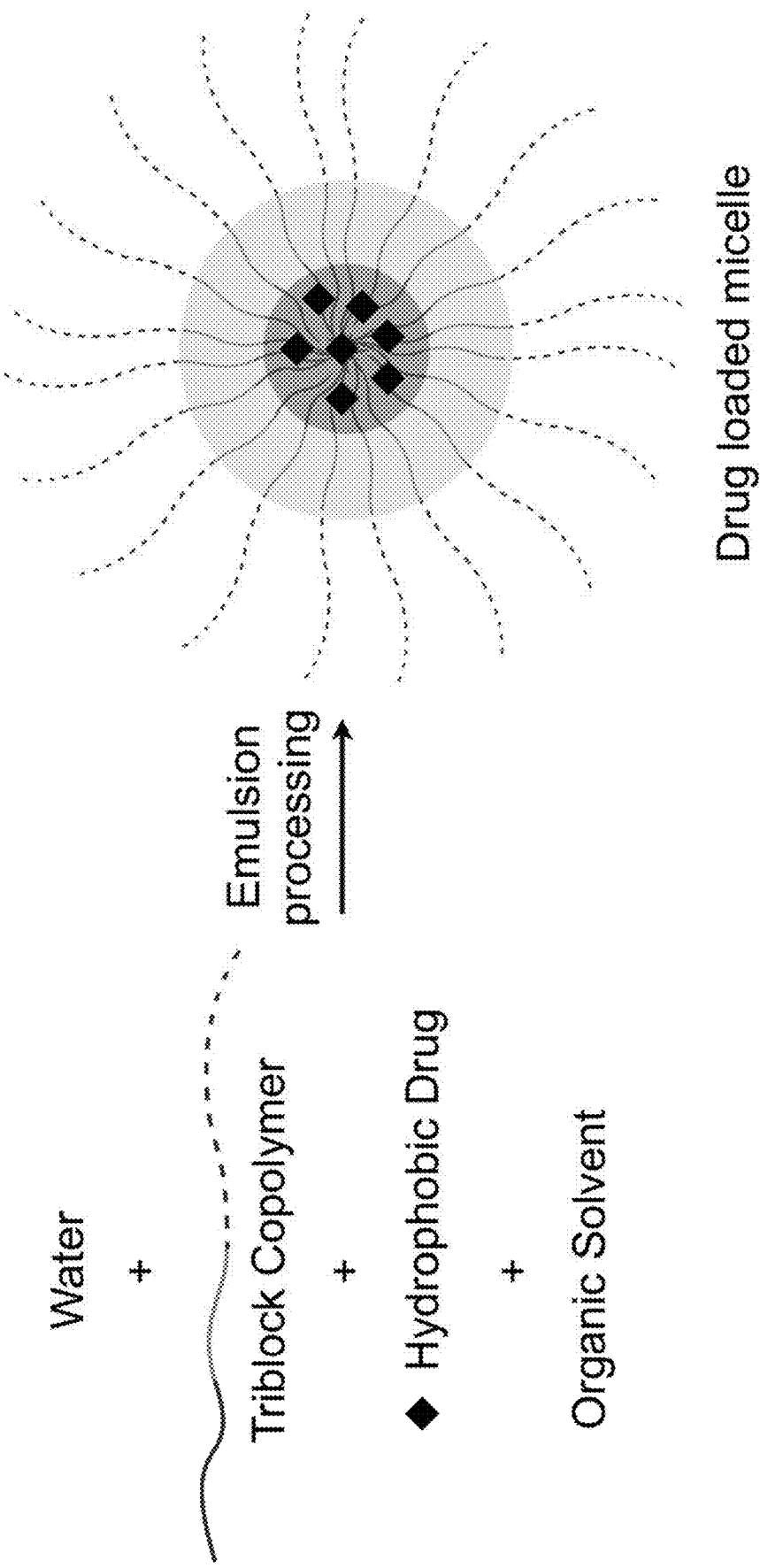
Figure 2. Drug Loaded Micelle Preparation

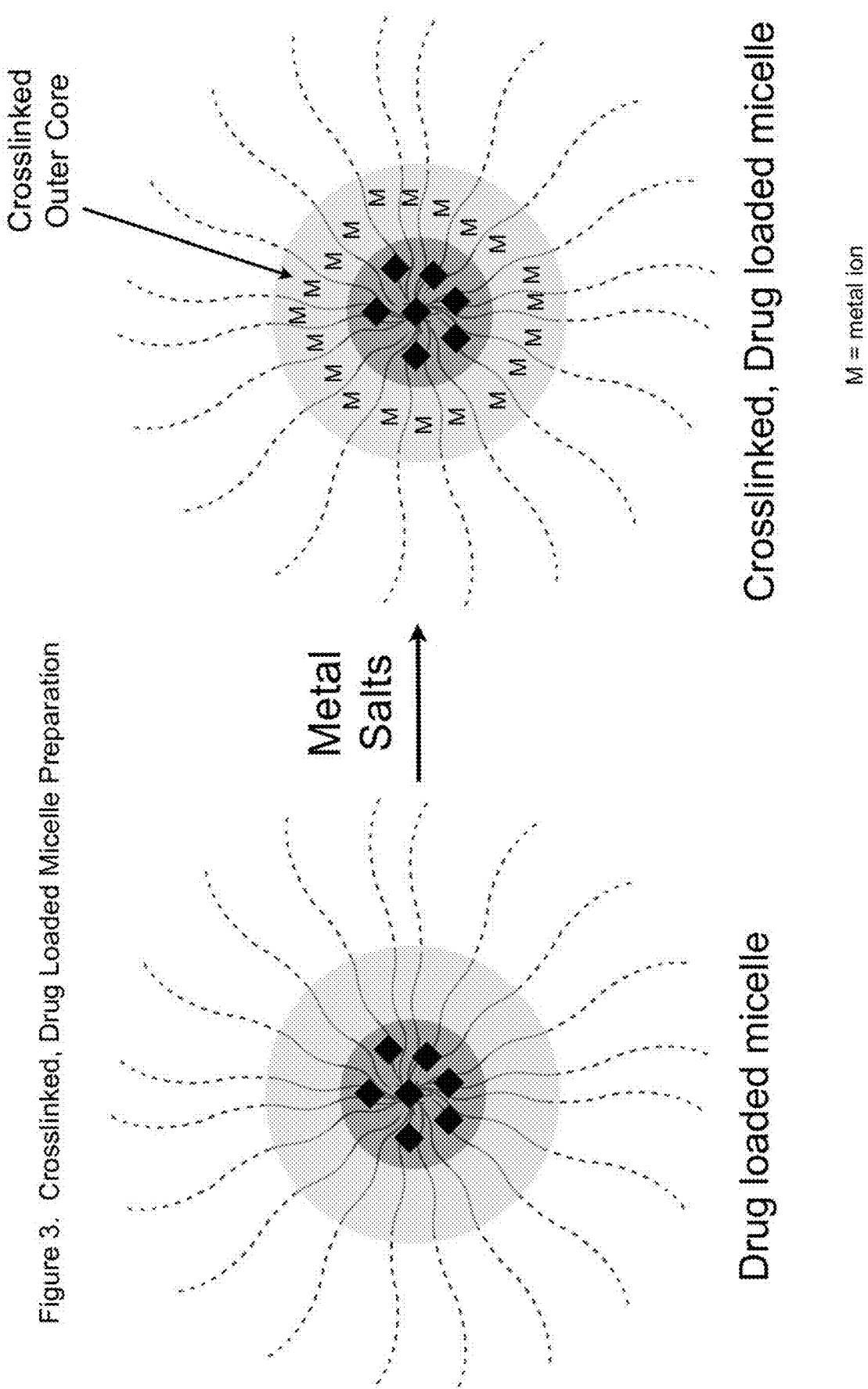
Figure 3. Crosslinked, Drug Loaded Micelle Preparation

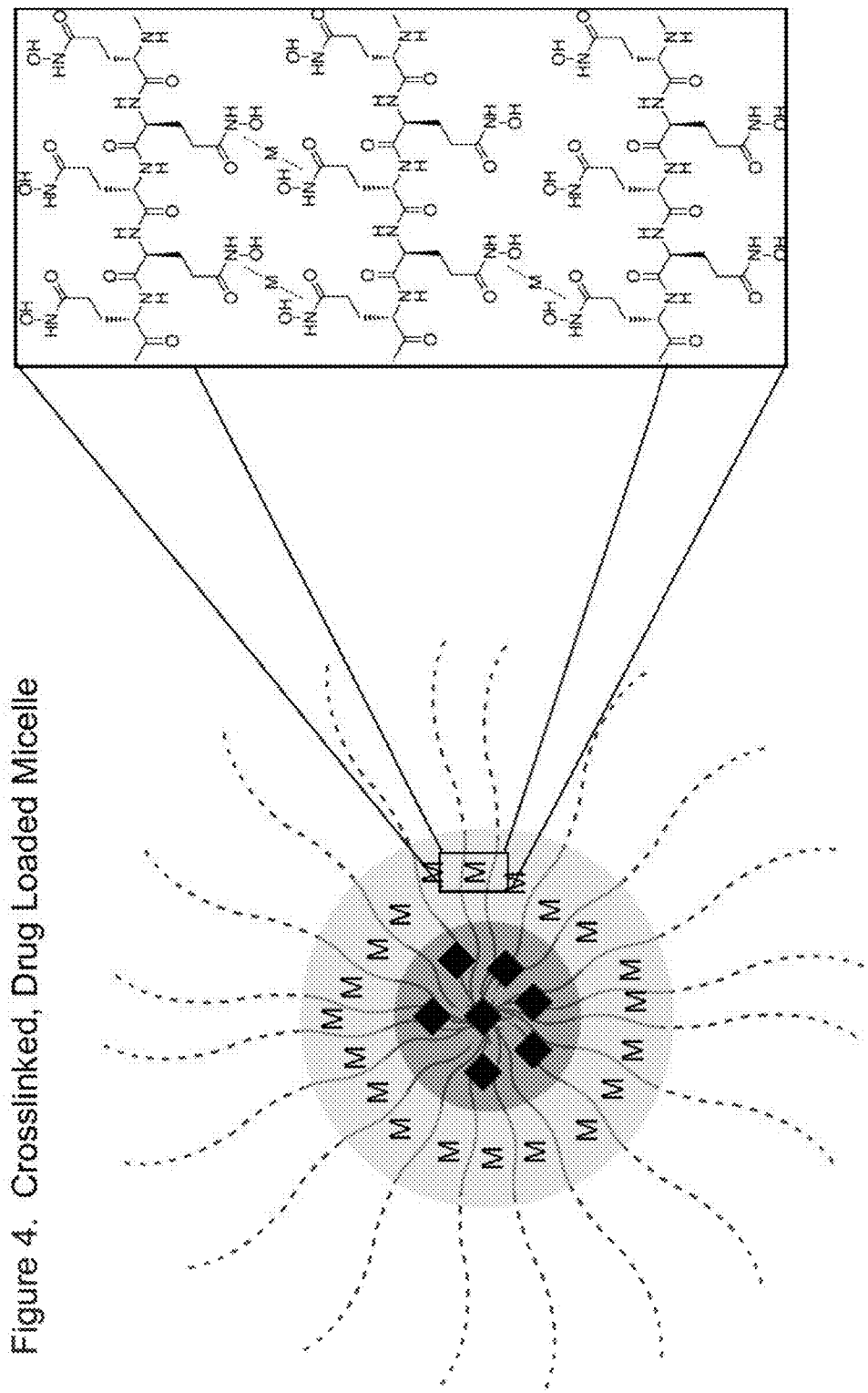
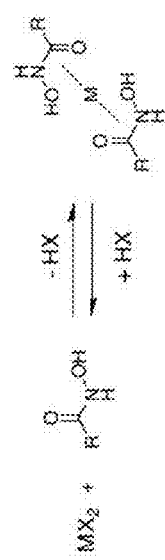
Figure 4. Crosslinked, Drug Loaded Micelle

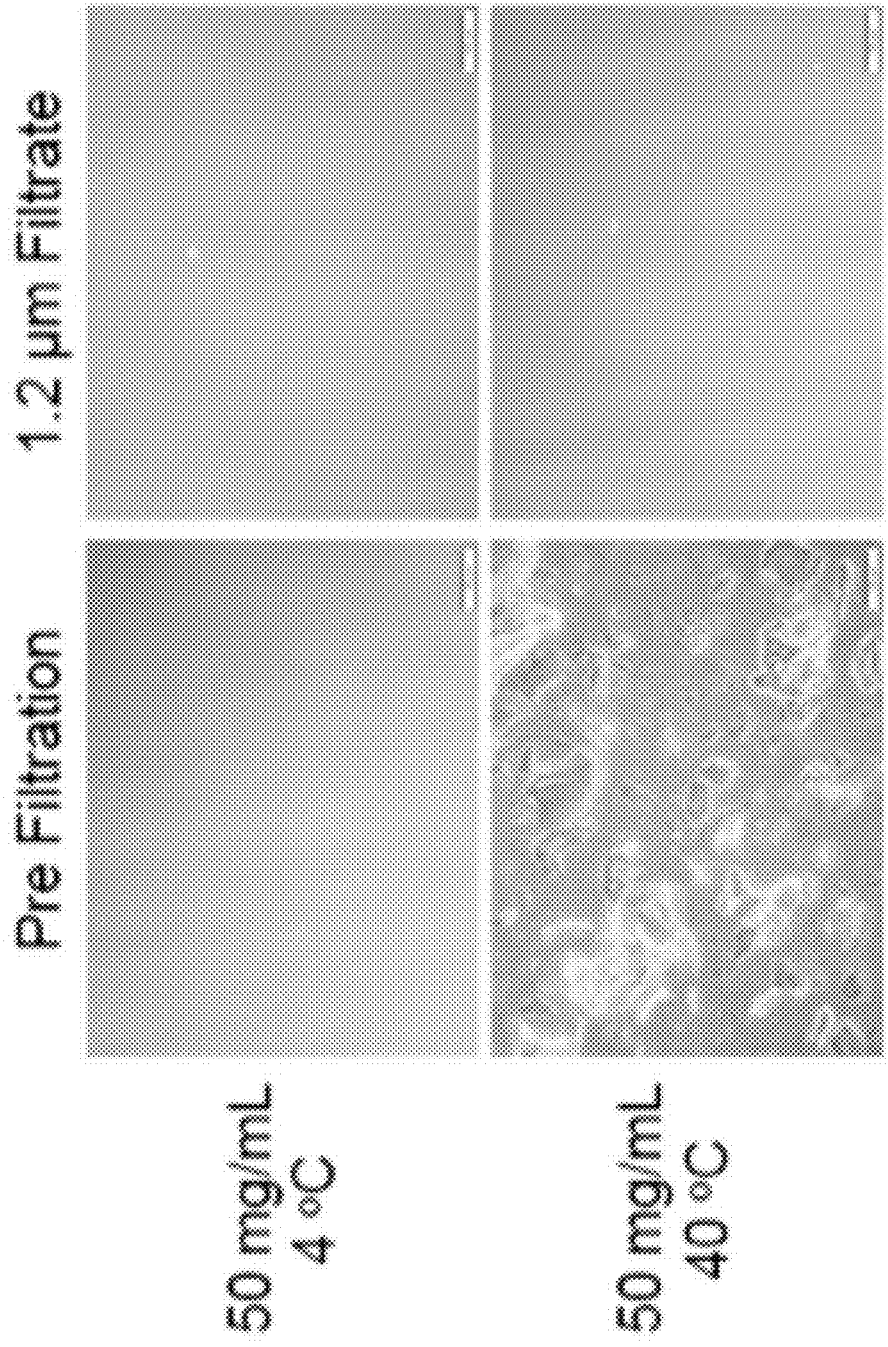
Figure 5. Optical micrographs of solutions of a formulation comprising SN-38, multiblock copolymer of Formula I, iron, and trehalose reconstituted with 4°C and 40°C saline before and after filtration through a 1.2 μm filter

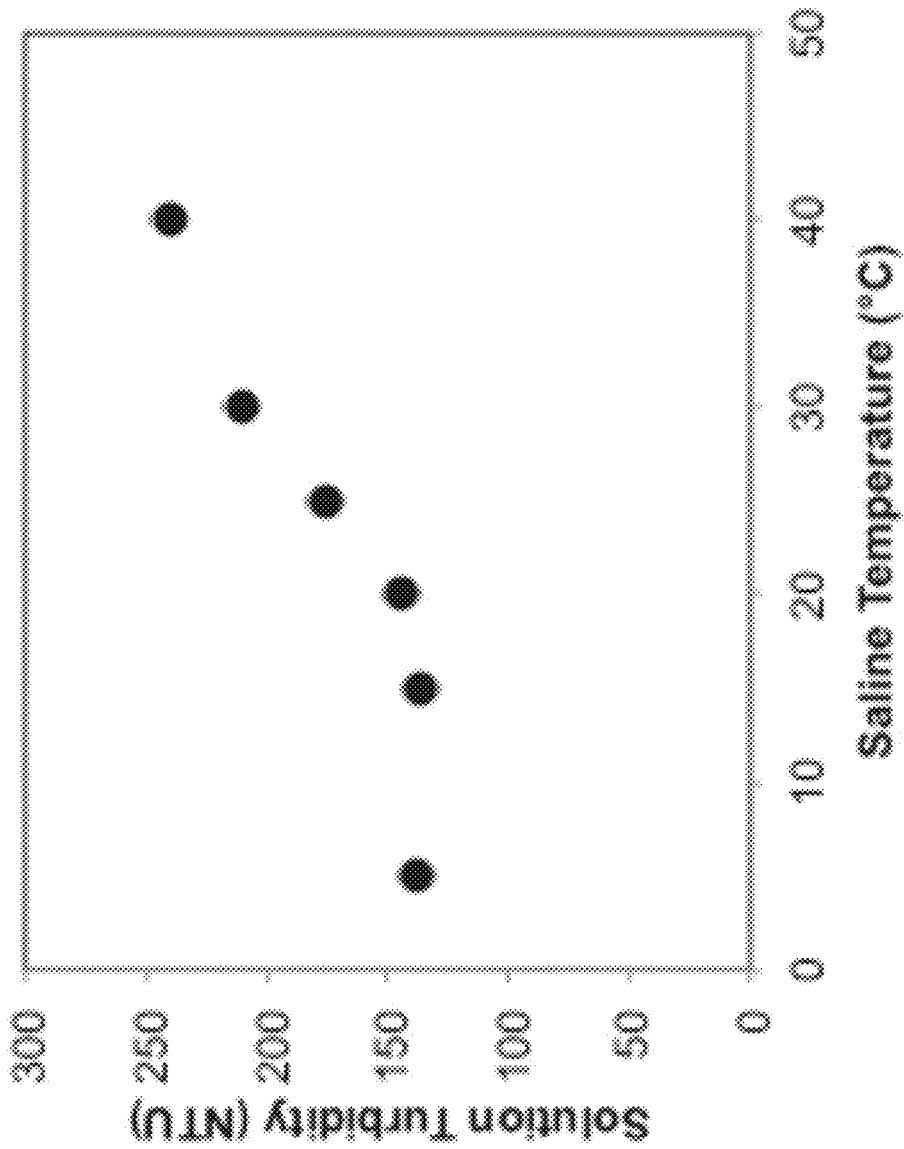

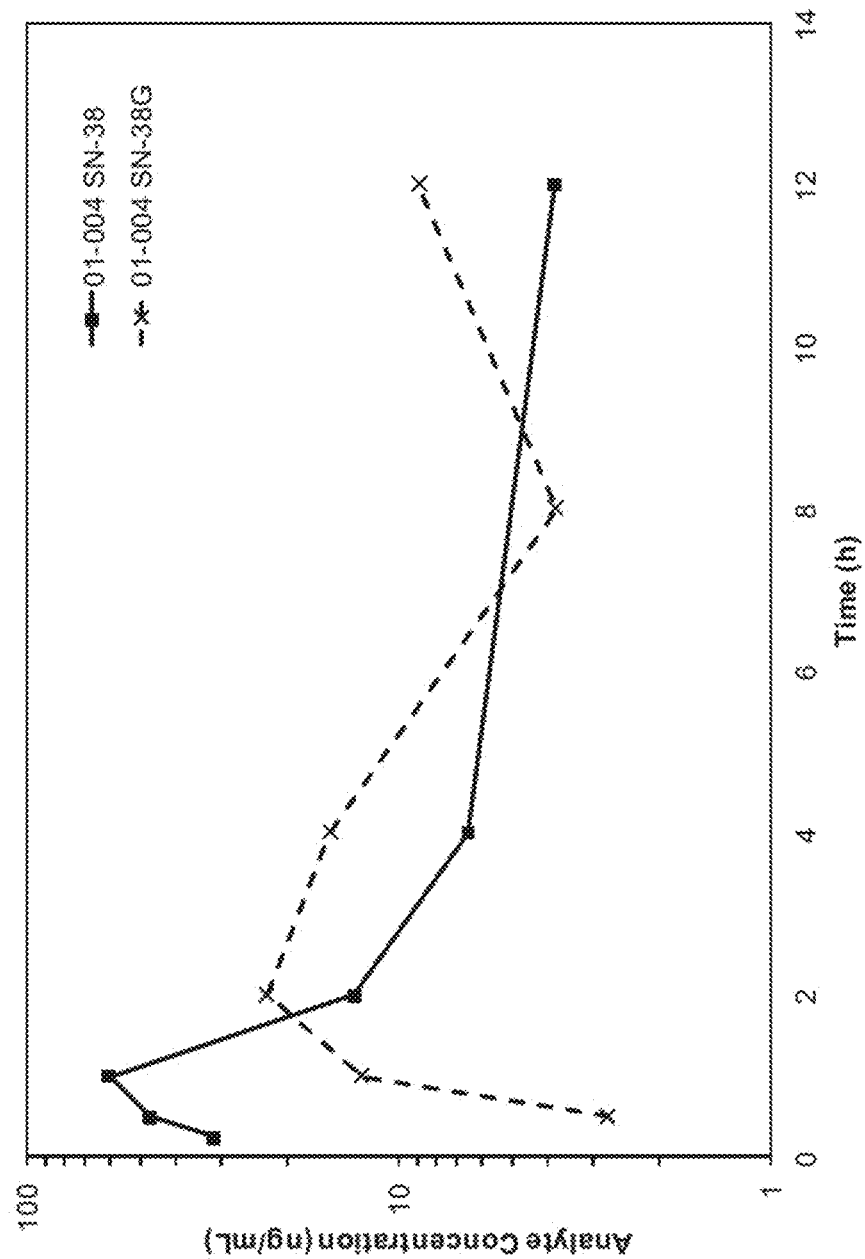
Figure 7. Plasma concentration of SN-38 and SN-38G following a 1 mg/m2 dose of IT-141 – Subject 004

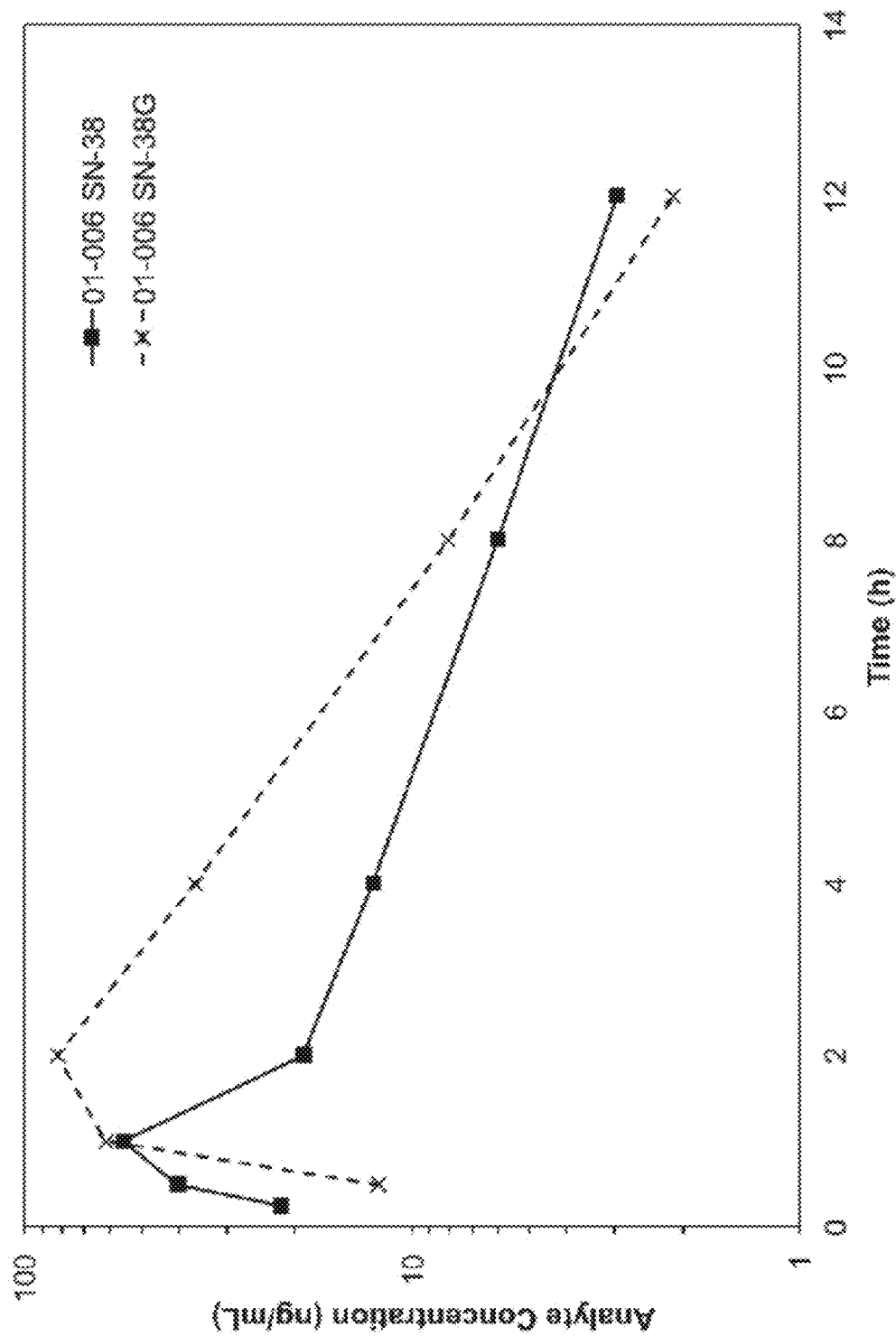
Figure 8. Plasma concentration of SN-38 and SN-38G following a 2 mg/m2 dose of IT-141 - Subject 006, cycle 1

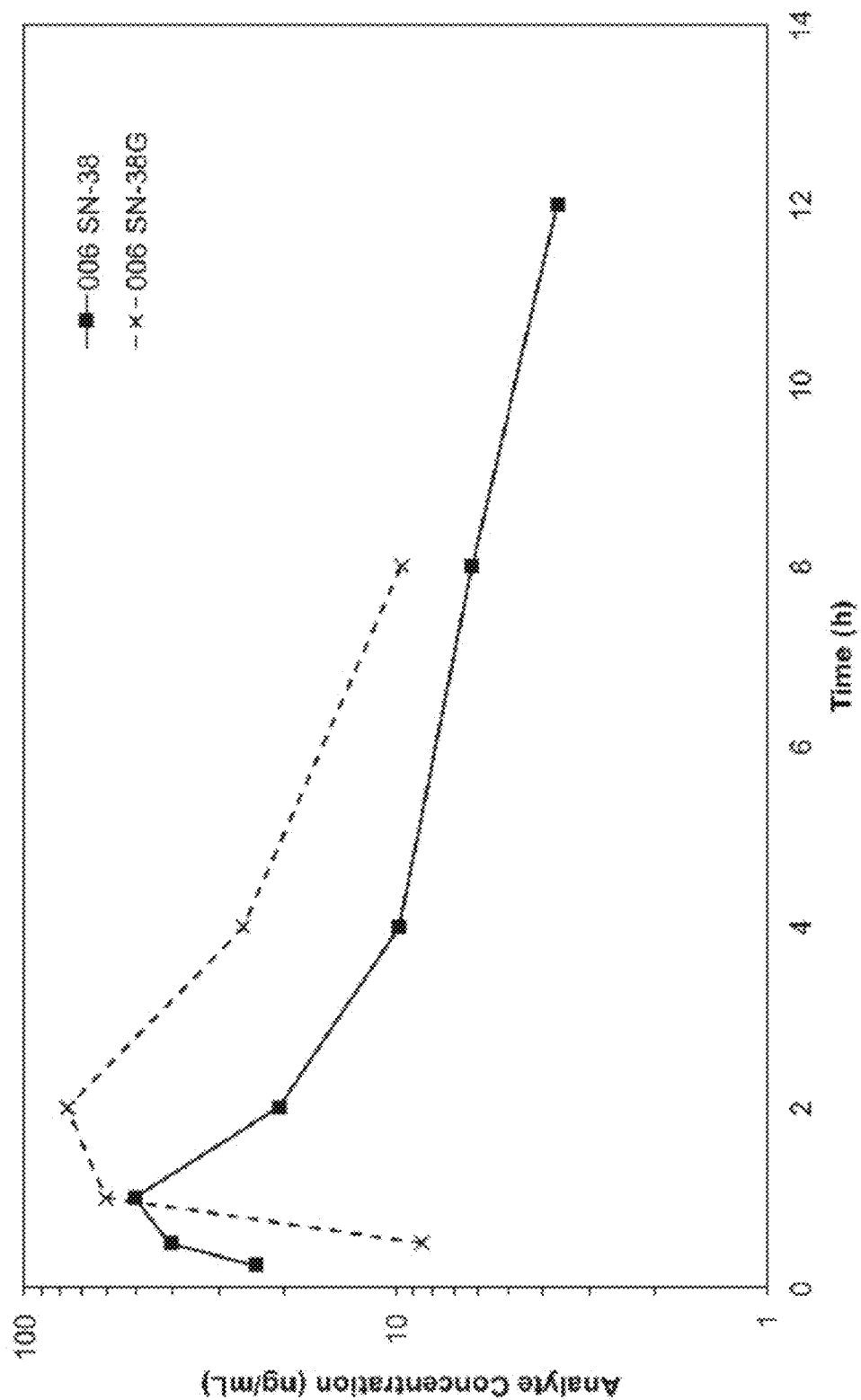
Figure 9. Plasma concentration of SN-38 and SN-38G following a 2 mg/m2 dose of IT-141 - Subject 006, cycle 2

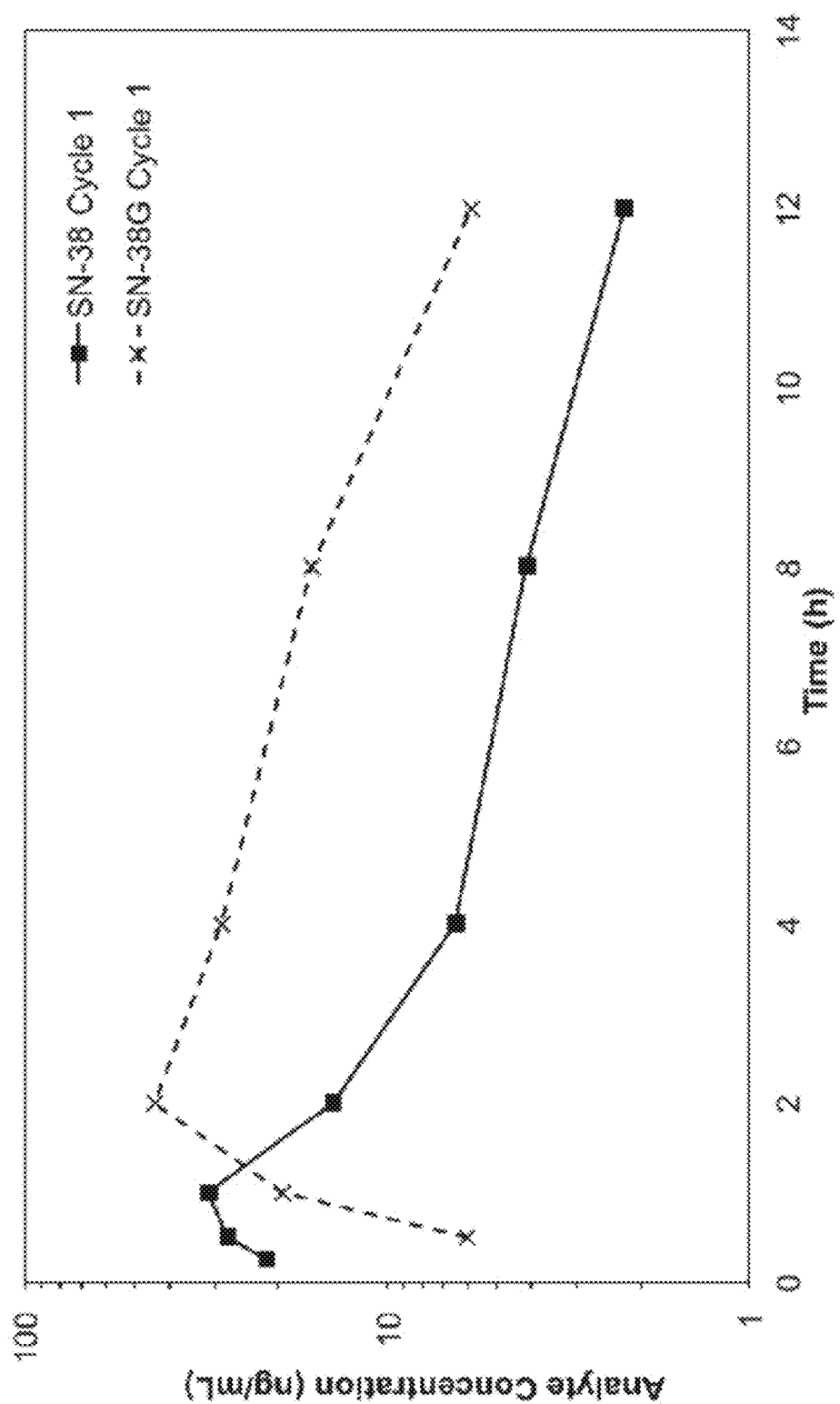
Figure 10. Plasma concentration of SN-38 and SN-38G following a 1 mg/m2 dose of IT-141 – Subject 007, cycle 1

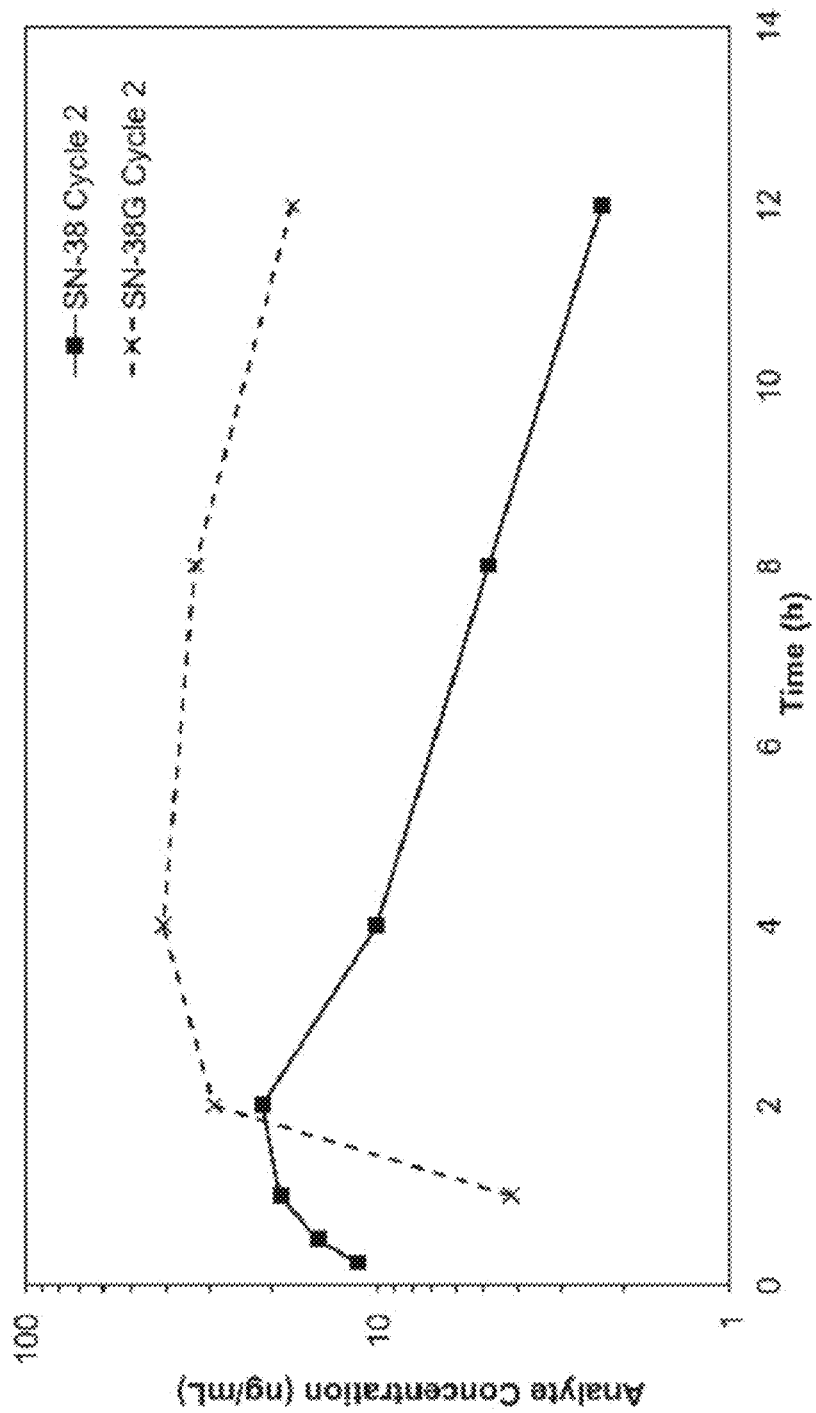
Figure 11. Plasma concentration of SN-38 and SN-38G following a 1 mg/m2 dose of IT-141 - Subject 007, cycle 2

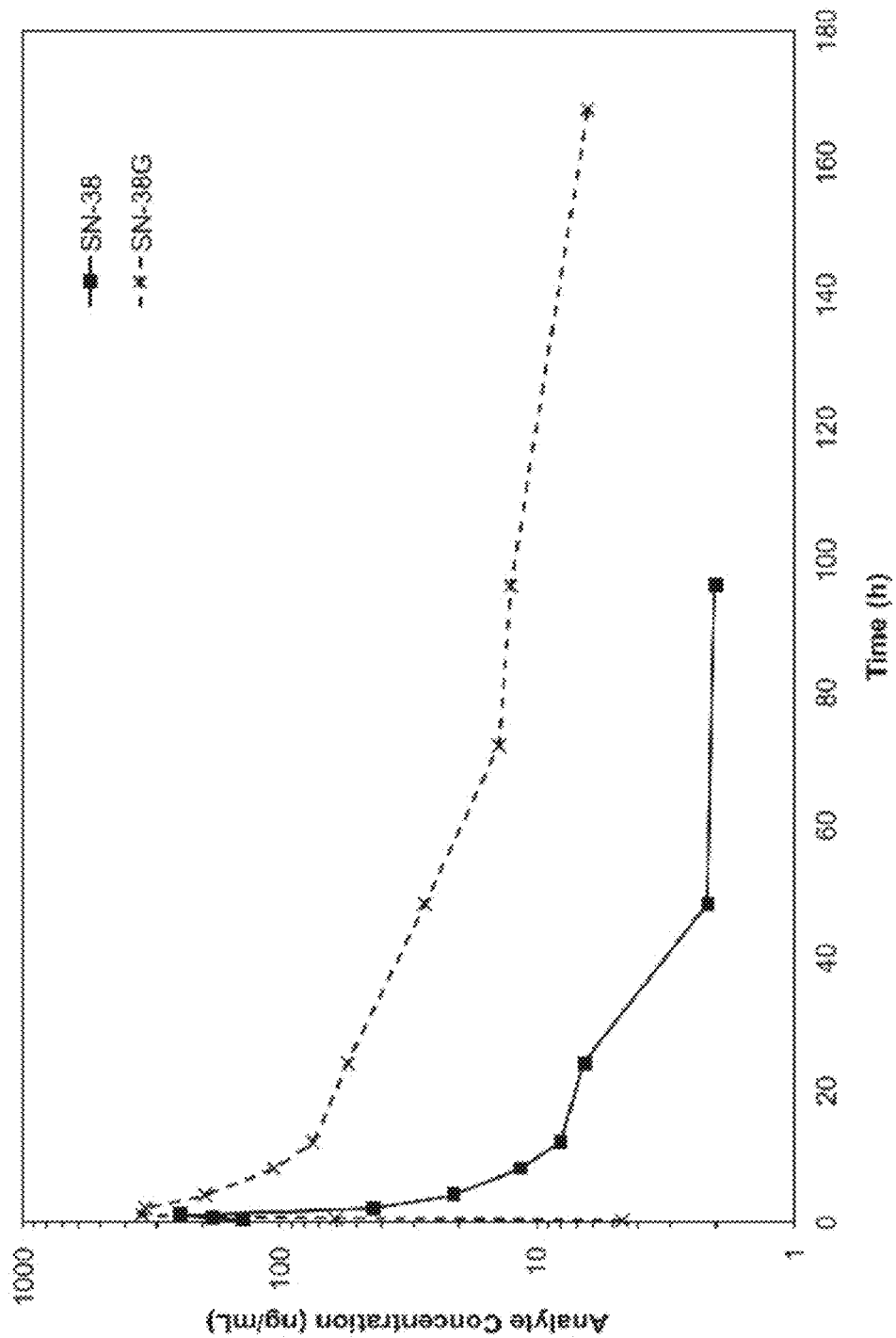
Figure 12. Plasma concentration of SN-38 and SN-38G following a 4 mg/m2 dose of IT-141 - Subject 008, cycle 1

SN-38 LOADED IRON CROSSLINKED MICELLE AND METHODS THEREOF

CROSS REFERENCE TO RELATED APPLICATIONS

This application claims the benefit of U.S. Provisional Application No. 62/456,396, filed Feb. 8, 2017, and U.S. Provisional Application No. 62/581,089, filed Nov. 3, 2017, the entirety of which are hereby incorporated herein by reference.

FIELD OF THE INVENTION

The present invention provides methods of treating, stabilizing, or lessening the severity or progression of proliferative diseases, such as cancer, with SN-38 encapsulated in a multiblock copolymer micelle crosslinked with iron.

BACKGROUND OF THE INVENTION

The antitumor plant alkaloid camptothecin (CPT) is a broad-spectrum anticancer agent that targets DNA topoisomerase I. Although CPT has shown promising antitumor activity in vitro and in vivo, it has not been clinically used because of its low therapeutic efficacy and severe toxicity. Among CPT analogues, irinotecan hydrochloride (CPT-11) has recently been shown to be active against colorectal, lung, and ovarian cancer. CPT-11 itself is a prodrug and is converted to 7-ethyl-10-hydroxy-CPT (known as SN-38), a biologically active metabolite of CPT-11, by carboxylesterases in vivo, having the following chemical structure:

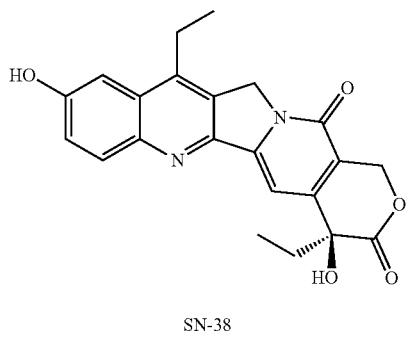 [SMILES: CCc1c2c(nc3ccc(O)cc13)-c1cc3c(c(=O)n1C2)COC(=O)[C@]3(O)CC ; "SN-38"]

SN-38

SN-38 exhibits up to 1,000-fold more potent cytotoxic activity against various cancer cells in vitro than CPT-11. Although CPT-11 is converted to SN-38 in the liver and tumor, the metabolic conversion rate is <10% of the original volume of CPT-11. In addition, the conversion of CPT-11 to SN-38 varies among patients due to inherent variations carboxylesterase activity. Thus, SN-38 has an advantage over its camptothecin precursors in that it does not require activation in vivo by the liver.

Notwithstanding the fact that SN-38 is more effective than CPT-11 as an antineoplastic agent, SN-38 is exceedingly insoluble in aqueous solutions. Therefore, no formulation for administration of SN-38 to a patient has yet been developed. Thus, formulations are needed that improve SN-38 efficacy such that SN-38 can be used effectively in the treatment of diseases associated with cellular proliferation. Such a formulation should have suitable solubility and toxicity characteristics and will be useful in the treatment of certain proliferative diseases such as cancer.

Rationally-designed, nanoscopic drug carriers, or "nanovectors," offer a promising approach to achieving these goals due to their inherent ability to overcome many biological barriers. Moreover, their multi-functionality permits the incorporation of cell-targeting groups, diagnostic agents, and a multitude of drugs in a single delivery system. Polymer micelles, formed by the molecular assembly of functional, amphiphilic block copolymers, represent one notable type of multifunctional nanovector.

Polymer micelles are particularly attractive due to their ability to deliver hydrophobic therapeutic agents. In addition, the nanoscopic size of polymeric micelles allows for passive accumulation in diseased tissues, such as solid tumors, by the enhanced permeation and retention (EPR) effect. Using appropriate surface functionality, polymer micelles are further decorated with cell-targeting groups and permeation enhancers that can actively target diseased cells and aid in cellular entry, resulting in improved cell-specific delivery.

Drug delivery vehicles are needed, which are stable to post-administration dilution, can avoid biological barriers (e.g. reticuloendothelial system (RES) uptake), and deliver drugs in response to the physiological environment encountered in diseased tissues, such as solid tumors.

The invention provides such a drug delivery method to deliver SN-38 for the treating, stabilizing, or lessening the severity or progression of proliferative diseases, such as cancer, with SN-38 encapsulated in a multiblock copolymer stabilized with iron.

These and other advantages of the present invention, as well as additional inventive features, will be apparent from the description of the invention provided herein.

BRIEF DESCRIPTION OF THE DRAWINGS

FIG. 1. Schematic illustrations depicting the triblock copolymer and polymer micelle of the present invention.

FIG. 2. Schematic illustrations showing the preparation of drug loaded micelles.

FIG. 3. Schematic illustrations showing the crosslinking of a drug loaded micelle with metal ions.

FIG. 4. Schematic illustrations depicting the crosslinked, drug loaded micelle of the present invention.

FIG. 5. Optical micrographs of solutions of a formulation comprising SN-38, multiblock copolymer of Formula I, iron, and trehalose reconstituted with 4° C. and 40° C. saline before and after filtration through a 1.2 μm filter.

FIG. 6. Effect of saline temperature on turbidity of a solution comprising SN-38, multiblock copolymer of Formula I, iron, and trehalose 1 minute after reconstitution of a lyophilized powder.

FIG. 7. Plasma concentration of SN-38 and SN-38G following a 1 mg/m$^2$ dose of IT-141—Subject 004.

FIG. 8. Plasma concentration of SN-38 and SN-38G following a 2 mg/m$^2$ dose of IT-141—Subject 006, cycle 1.

FIG. 9. Plasma concentration of SN-38 and SN-38G following a 2 mg/m$^2$ dose of IT-141—Subject 006, cycle 2.

FIG. 10. Plasma concentration of SN-38 and SN-38G following a 1 mg/m$^2$ dose of IT-141—Subject 007, cycle 1.

FIG. 11. Plasma concentration of SN-38 and SN-38G following a 1 mg/m$^2$ dose of IT-141—Subject 007, cycle 2.

FIG. 12. Plasma concentration of SN-38 and SN-38G following a 4 mg/m$^2$ dose of IT-141—Subject 008, cycle 1.

DETAILED DESCRIPTION OF CERTAIN EMBODIMENTS OF THE INVENTION

1. General Description

According to one embodiment, the present invention provides methods of treating, stabilizing, or lessening the severity or progression of proliferative diseases, such as cancer, with a pharmaceutically acceptable composition comprising a multiblock copolymer having SN-38 encapsulated therein, stabilized with iron.

SN-38 is a the active metabolite of CPT-11 (irinotecan) is known to comprising impurities including, but not limited to, 7-ethyl camptothecin, 10-hydroxy camptothecin, and 10-hydroxy-7-methyl camptothecin According to one embodiment, the present invention provides a micelle comprising a multiblock copolymer which comprises a polymeric hydrophilic block, optionally a crosslinkable or crosslinked poly(amino acid block), and a hydrophobic D,L-mixed poly(amino acid) block, characterized in that said micelle has an inner core, optionally a crosslinkable or crosslinked outer core, and a hydrophilic shell. It will be appreciated that the polymeric hydrophilic block corresponds to the hydrophilic shell, the optionally crosslinkable or crosslinked poly(amino acid block) corresponds to the optionally crosslinked outer core, and the hydrophobic D,L-mixed poly(amino acid) block corresponds to the inner core.

The "hydrophobic D,L-mixed poly(amino acid)" block, as described herein, consists of a mixture of D and L enantiomers to facilitate the encapsulation of hydrophobic moieties. It is well established that homopolymers and copolymers of amino acids, consisting of a single stereoisomer, may exhibit secondary structures such as the α-helix or β-sheet. See α-*Aminoacid-N-Caroboxy-Anhydrides and Related Heterocycles*, H. R. Kricheldorf, Springer-Verlag, 1987. For example, poly(L-benzyl glutamate) typically exhibits an α-helical conformation; however this secondary structure can be disrupted by a change of solvent or temperature (see *Advances in Protein Chemistry XVI*, P. Urnes and P. Doty, Academic Press, New York 1961). The secondary structure can also be disrupted by the incorporation of structurally dissimilar amino acids such as β-sheet forming amino acids (e.g. proline) or through the incorporation of amino acids with dissimilar stereochemistry (e.g. mixture of D and L stereoisomers), which results in poly(amino acids) with a random coil conformation. See Sakai, R.; Ikeda; S.; Isemura, T. *Bull Chem. Soc. Japan* 1969, 42, 1332-1336, Paolillo, L.; Temussi, P. A.; Bradbury, E. M.; Crane-Robinson, C. *Biopolymers* 1972, 11, 2043-2052, and Cho, I.; Kim, J. B.; Jung, H. J. *Polymer* 2003, 44, 5497-5500.

While the methods to influence secondary structure of poly(amino acids) have been known for some time, it has been surprisingly discovered that block copolymers possessing a random coil conformation are particularly useful for the encapsulation of hydrophobic molecules and nanoparticles when compared to similar block copolymers possessing a helical segment. See US Patent Application 2008-0274173. Without wishing to be bound to any particular theory, it is believed that provided block copolymers having a coil-coil conformation allow for efficient packing and loading of hydrophobic moieties within the micelle core, while the steric demands of a rod-coil conformation for a helix-containing block copolymer results in less effective encapsulation.

The hydrophobic forces that drive the aqueous assembly of colloidal drug carriers, such as polymer micelles and liposomes, are relatively weak, and these assembled structures dissociate below a finite concentration known as the critical micelle concentration (CMC). The CMC value of polymer micelles is of great importance in clinical applications because drug-loaded colloidal carriers are diluted in the bloodstream following administration and rapidly reach concentrations below the CMC (μM or less). This dilution effect will lead to micelle dissociation and drug release outside the targeted area and any benefits associated with the micelle size (EPR effect) or active targeting will be lost. While a great deal of research throughout the 1990's focused on identifying polymer micelles with ultra-low CMC values (nM or less), Maysinger (Savic et. al., *Langmuir*, 2006, p 3570-3578) and Schiochet (Lu et. al., *Macromolecules*, 2011, p 6002-6008) have redefined the concept of a biologically relevant CMC by showing that the CMC values for polymer micelles shift by two orders of magnitude when the CMC values in saline are compared with and without serum.

In addition to their core-shell morphology, polymer micelles can be modified to enable passive and active cell-targeting to maximize the benefits of current and future therapeutic agents. Because drug-loaded micelles typically possess diameters greater than 20 nm, they exhibit dramatically increased circulation time when compared to stand-alone drugs due to minimized renal clearance. This unique feature of nanovectors and polymeric drugs leads to selective accumulation in diseased tissue, especially cancerous tissue due to the enhanced permeation and retention effect ("EPR"). The EPR effect is a consequence of the disorganized nature of the tumor vasculature, which results in increased permeability of polymer therapeutics and drug retention at the tumor site. In addition to passive cell targeting by the EPR effect, micelles are designed to actively target tumor cells through the chemical attachment of targeting groups to the micelle periphery. The incorporation of such groups is most often accomplished through end-group functionalization of the hydrophilic block using chemical conjugation techniques. Like viral particles, micelles functionalized with targeting groups utilize receptor-ligand interactions to control the spatial distribution of the micelles after administration, further enhancing cell-specific delivery of therapeutics. In cancer therapy, targeting groups are designed to interact with receptors that are over-expressed in cancerous tissue relative to normal tissue such as folic acid, oligopeptides, sugars, and monoclonal antibodies. See Pan, D.; Turner, J. L.; Wooley, K. L. *Chem. Commun.* 2003, 2400-2401; Gabizon, A.; Shmeeda, H.; Horowitz, A. T.; Zalipsky, S. *Adv. Drug Deliv. Rev.* 2004, 56, 1177-1202; Reynolds, P. N.; Dmitriev, I.; Curiel, D. T. *Vector. Gene Ther.* 1999, 6, 1336-1339; Derycke, A. S. L.; Kamuhabwa, A.; Gijsens, A.; Roskams, T.; De Vos, D.; Kasran, A.; Huwyler, J.; Missiaen, L.; de Witte, P. A. M. T *J. Nat. Cancer Inst.* 2004, 96, 1620-30; Nasongkla, N., Shuai, X., Ai, H.; Weinberg, B. D. P., J.; Boothman, D. A.; Gao, J. *Angew. Chem. Int. Ed.* 2004, 43, 6323-6327; Jule, E.; Nagasaki, Y.; Kataoka, K. *Bioconj. Chem.* 2003, 14, 177-186; Stubenrauch, K.; Gleiter, S.; Brinkmann, U.; Rudolph, R.; Lilie, H. *Biochem. J.* 2001, 356, 867-873; Kurschus, F. C.; Kleinschmidt, M.; Fellows, E.; Dornmair, K.; Rudolph, R.; Lilie, H.; Jenne, D. E. *FEBS Lett.* 2004, 562, 87-92; and Jones, S. D.; Marasco, W. A. *Adv. Drug Del. Rev.* 1998, 31, 153-170.

Despite the large volume of work on micellar drug carriers, little effort has focused on improving their in vivo stability to dilution. One potential reason is that the true effects of micelle dilution in vivo are not fully realized until larger animal studies are utilized. Because a mouse's metabolism is much higher than larger animals, they can receive considerably higher doses of toxic drugs when compared to larger animals such as rats or dogs. Therefore, when drug loaded micelles are administered and completely severity or progression of proliferative diseases, such as cancer, with a pharmaceutically acceptable composition comprising a multiblock copolymer of Formula I crosslinked with iron having SN-38 encapsulated therein.

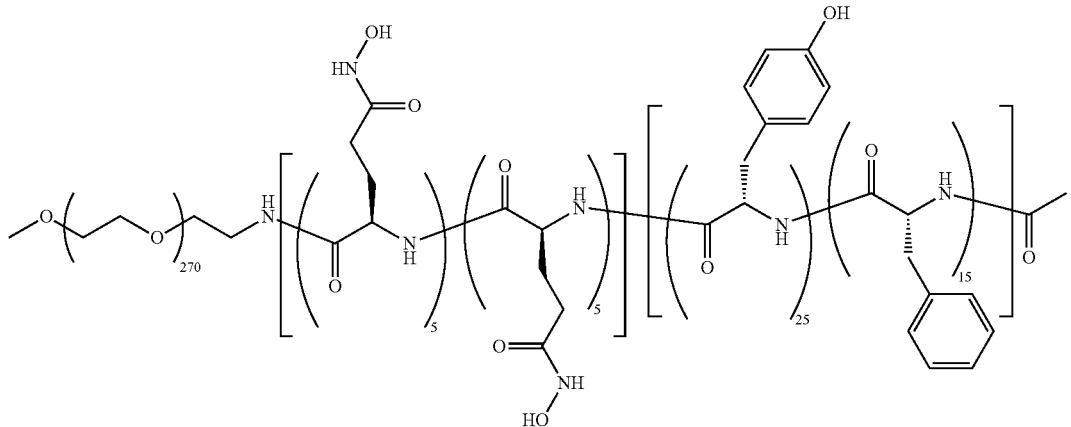

Formula I diluted throughout the entire blood volume, the corresponding polymer concentration will always be highest in the mouse model. Therefore, it would be highly desirable to prepare a micelle that is stabilized (crosslinked) to dilution within biological media.

In the present invention, the optionally crosslinkable or crosslinked poly(amino acid block) is comprised of chemical functionality that strongly binds or coordinates with metal ions. One specific example is hydroxamic acids and iron (III). Another example is ortho-substituted dihydroxy benzene groups (catechols) with iron. Both hydroxamic acid and catechol moieties are common in siderophores, high-affinity iron chelating agents produced by microorganisms. Additionally, it has been reported that hydroxamic acid modified poly(acrylates) can form a crosslinked gel following treatment with iron (III) (Rosthauser and Winston, *Macromolecules*, 1981, p 538-543). Without wishing to be bound to any particular theory, it is believed that the incorporation of high affinity metal chelating group such as hydroxamic acids and catechols in the outer core of the micelle, following treatment with a metal ion will result in a micelle that is stable to dilution within biological media.

Previous work has utilized carboxylic acids to interact with metal ions in order to provide micelle stability. See US Patent Application 2006-0240092. It has been surprisingly discovered that the use of hydroxamic acid-modified polymers is effective at reversibly stabilizing the polymer micelle to dilution within biological media. This hydroxamic acid chemistry has been demonstrated to be particularly effective when encapsulating a drug that possesses one or more chemical functionalities known to bind iron (e.g. carboxylic acids). Without wishing to be bound to any particular theory, it is believed that the metal ions used to stabilize the micelle will preferentially bind to the high affinity metal chelating group such as hydroxamic acids and catechols, resulting in a stabilized micelle. Furthermore, the chelation reaction between iron (III) and hydroxamic acid moieties proceeds within seconds, allowing for a rapid crosslinking step.

According to one embodiment, the present invention provides methods of treating, stabilizing, or lessening the Formula I of the present invention is multiblock copolymer (methoxy-poly(ethylene glycol)-block-poly[(D-glutamic acid γ-hydroxamate)-co-(L-glutamic acid γ-hydroxamate)]-block-poly(L-tyrosine-co-D-phenylalanine)-acetamide), and is described in U.S. Pat. No. 9,078,930 (referred herein as "the '930 patent"; published on Oct. 24, 2013 as U.S. patent application serial number 2013/0280306 A1), and in U.S. patent application Ser. No. 14/028,485 (referred herein as "the 485 application"; published May 8, 2014 as US 2014-0127271), the entirety of which is hereby incorporated herein by reference.

In certain embodiments, the present invention provides a method to encapsulate SN-38 in a polymeric micelle comprising multiblock copolymer of Formula I stabilized with iron. The method of encapsulation is described in the '930 patent. The iron-stabilized micelle is depicted in FIG. 4.

In some embodiments, the present invention provides methods of treating, stabilizing or lessening the severity or progression of a proliferative disorder, wherein the method comprises administering to a patient in need thereof a pharmaceutically acceptable composition comprising SN-38, encapsulated in multiblock copolymer of Formula I, and cross-linked with iron.

In some embodiments, the cancer is a locally advanced cancer. In some embodiments, the cancer is metastatic. In some embodiments, the cancer is recurring. In some embodiments, the cancer is refractory.

In some embodiments, the cancer is selected from multiple myeloma, breast, ovary, cervix, prostate, testis, genitourinary tract, esophagus, larynx, glioblastoma, neuroblastoma, stomach (gastric), skin, keratoacanthoma, lung, epidermoid carcinoma, large cell carcinoma, small cell carcinoma, lung, bone, colon, thyroid, adenoma, pancreas, adenocarcinoma, thyroid, follicular carcinoma, undifferentiated carcinoma, papillary carcinoma, seminoma, melanoma (including uveal melanoma) sarcoma, bladder carcinoma, liver carcinoma (e.g., hepatocellular carcinoma (HCC)) and biliary passages, kidney carcinoma, myeloid disorders, lymphoid disorders, Hodgkin's disease, hairy cells, buccal cavity and pharynx (oral), lip, tongue, mouth, pharynx, small intestine, colorectal carcinoma, large intestine, rectum, brain and central nervous system, endometrial, multiple myeloma (MM), prostate, acute myeloid leukemia (AML), and leukemia. In some such embodiments, the cancer is relapsed. In some embodiments, the cancer is refractory. In some embodiments, the cancer is locally advanced. In some embodiments, the cancer is metastatic.

In some embodiments, the cancer is selected from carcinoma, lymphoma, blastoma, sarcoma, and leukemia. In some embodiments, a sarcoma is a soft tissue sarcoma. In some embodiments, a lymphoma is non-Hodgkin's lymphoma. In some embodiments, a lymphoma is large cell immunoblastic lymphoma. In some embodiments, the cancer is selected from adenocarcinoma; adenoma; adrenocortical cancer; bladder cancer; bone cancer; brain cancer; breast cancer; cancer of the buccal cavity; cervical cancer; colon cancer; colorectal cancer; endometrial or uterine carcinoma; epidermoid carcinoma; esophageal cancer; eye cancer; follicular carcmoma; gallbladder cancer; prostate, AML, multiple myeloma (MM), gastrointestinal cancer, such as, for example, gastrointestinal stromal tumor; cancer of the genitourinary tract; glioblastoma; hairy cell carcinoma; various types of head and neck cancer; hepatic carcinoma; hepatocellular cancer; Hodgkin's disease; keratoacanthoma; kidney cancer; large cell carcinoma; cancer of the large intestine; laryngeal cancer; liver cancer; lung cancer, such as, for example, adenocarcinoma of the lung, anaplastic carcinoma of the lung, papillary lung adenocarcinoma, small-cell lung cancer, squamous carcinoma of the lung, non-small cell lung cancer; melanoma and nonmelanoma skin cancer; lymphoid disorders; myeloproliferative disorders, such as, for example, polycythemia vera, essential thrombocythemia, chronic idiopathic myelofibrosis, myeloid metaplasia with myelofibrosis, chronic myeloid leukemia (CML), chronic myelomonocytic leukemia, chronic eosinophilic leukemia, chronic lymphocytic leukemia (CLL), hypereosinophilic syndrome, systematic mast cell disease, atypical CML, AML, or juvenile myelomonocytic leukemia; plasmacytoma; multiple myeloma; neuroblastoma; ovarian cancer; papillary carcinoma; pancreatic cancer; cancer of the peritoneum; prostate cancer, including benign prostatic hyperplasia; rectal cancer; salivary gland carcinoma; sarcoma; seminoma; squamous cell cancer; small cell carcinoma; cancer of the small intestine; stomach cancer; testicular cancer; thyroid cancer; undifferentiated carcinoma; and vulval cancer. In some such embodiments, the cancer is relapsed. In some embodiments, the cancer is refractory. In some embodiments, the cancer is locally advanced. In some embodiments, the cancer is metastatic.

In certain embodiments, the cancer is selected from melanoma, pancreatic cancer, thyroid cancer, colorectal cancer, lung cancer (e.g., non-small cell lung cancer), breast cancer, endometrial cancer, prostate cancer, ovarian cancer, hepatocellular carcinoma (HCC), multiple myeloma (MM), and leukemia. In some embodiments, a leukemia is an acute leukemia. In certain embodiments, a leukemia is acute myeloid leukemia. In certain embodiments, a leukemia is acute lymphoblastic leukemia.

In some embodiments, the cancer is selected from melanoma, colorectal cancer, lung cancer, or pancreatic.

In certain embodiments, the cancer is a leukemia. In some embodiments, a leukemia is a chronic leukemia. In certain embodiments, a leukemia is chronic myeloid leukemia. In some embodiments, a leukemia is an acute leukemia. In certain embodiments, a leukemia is acute myeloid leukemia (AML). In certain embodiments, a leukemia is acute monocytic leukemia (AMoL, or AML-M5). In certain embodiments, a leukemia is acute lymphoblastic leukemia (ALL). In certain embodiments, a leukemia is acute T cell leukemia.

In certain embodiments, a leukemia is myelomonoblastic leukemia. In certain embodiments, a leukemia is human B cell precursor leukemia. In certain embodiments, a leukemia has a Flt3 mutation or rearrangement. In some embodiments, the leukemia is relapsed. In some embodiments, the leukemia is refractory.

In some embodiments, the cancer is a CNS cancer, for instance CNS tumors. In certain embodiments, a CNS tumor is a glioblastoma or glioblastoma multiforme (GBM). In some embodiments, the present invention provides a method of treating stomach (gastric) and esophageal tumors and cancers.

In some embodiments, the cancer is selected from melanoma, colorectal cancer, lung cancer, or pancreatic cancer.

In some embodiments, the provided methods comprise parenteral administration to a patient a pharmaceutically acceptable composition comprising a multiblock copolymer of Formula I having SN-38 encapsulated therein, stabilized with iron. In general, provided methods comprise administering a composition which comprises a multiblock copolymer of Formula I having SN-38 encapsulated, and one or more pharmaceutically acceptable excipients, such as, for example, a stabilizing agent, and/or a cryoprotectants.

2. Definitions

Compounds of this invention include those described generally above, and are further illustrated by the embodiments, sub-embodiments, and species disclosed herein. As used herein, the following definitions shall apply unless otherwise indicated.

As used herein, the term "multiblock copolymer" refers to a polymer comprising one synthetic polymer portion and two or more poly(amino acid) portions. Such multi-block copolymers include those having the format W-X'-X", wherein W is a synthetic polymer portion and X and X' are poly(amino acid) chains or "amino acid blocks". In certain embodiments, the multiblock copolymers of the present invention are triblock copolymers. As described herein, one or more of the amino acid blocks may be "mixed blocks", meaning that these blocks can contain a mixture of amino acid monomers thereby creating multiblock copolymers of the present invention. In some embodiments, the multiblock copolymers of the present invention comprise a mixed amino acid block and are tetrablock copolymers One skilled in the art will recognize that a monomer repeat unit is defined by parentheses depicted around the repeating monomer unit. The number (or letter representing a numerical range) on the lower right of the parentheses represents the number of monomer units that are present in the polymer chain. In the case where only one monomer represents the block (e.g. a homopolymer), the block will be denoted solely by the parentheses. In the case of a mixed block, multiple monomers comprise a single, continuous block. It will be understood that brackets will define a portion or block. For example, one block may consist of four individual monomers, each defined by their own individual set of parentheses and number of repeat units present. All four sets of parentheses will be enclosed by a set of brackets, denoting that all four of these monomers combine in random, or near random, order to comprise the mixed block. For clarity, the randomly mixed block of [BCADDCBAD-ABCDABC] would be represented in shorthand by [(A)$_4$(B)$_4$(C)$_4$(D)$_4$].

As used herein, the term "triblock copolymer" refers to a polymer comprising one synthetic polymer portion and two poly(amino acid) portions.

As used herein, a "drug product" means a therapeutic agent, and one or more excipients selected from, but not limited to, tonicity agents, cryoprotectants, multiblock copolymers, stabilizing agents, antiadherents, binders, coatings, colors, disintegrants, flavors, glidants, lubricants, preservatives, sorbents, sweeteners, and vehicles. As appreciated by those skilled in the art, the amounts of each excipient will depend on the therapeutic agent, the route of administration, the desired biological endpoint, the target cell or tissue.

As used herein, a "therapeutically effective amount" means an amount of a substance (e.g., a therapeutic agent, composition, and/or formulation) that elicits a desired biological response. In some embodiments, a therapeutically effective amount of a substance is an amount that is sufficient, when administered as part of a dosing regimen to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a "therapeutically effective amount" is at least a minimal amount of a compound, or composition containing a compound, which is sufficient for treating one or more symptoms of a disease or disorder associated with proliferative diseases, such as cancer.

The term "subject", as used herein, means a mammal and includes human and animal subjects, such as domestic animals (e.g., horses, dogs, cats, etc.).

The terms "treat" or "treating," as used herein, refers to partially or completely alleviating, inhibiting, delaying onset of, preventing, ameliorating and/or relieving a disease or disorder, or one or more symptoms of the disease or disorder. As used herein, the terms "treatment," "treat," and "treating" refer to partially or completely alleviating, inhibiting, delaying onset of, preventing, ameliorating and/or relieving a disease or disorder, or one or more symptoms of the disease or disorder, as described herein. In some embodiments, treatment may be administered after one or more symptoms have developed. In some embodiments, the term "treating" includes preventing or halting the progression of a disease or disorder. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence. Thus, in some embodiments, the term "treating" includes preventing relapse or recurrence of a disease or disorder The expression "unit dosage form" as used herein refers to a physically discrete unit of inventive formulation appropriate for the subject to be treated. It will be understood, however, that the total daily usage of the compositions of the present invention will be decided by the attending physician within the scope of sound medical judgment. The specific effective dose level for any particular subject or organism will depend upon a variety of factors including the disorder being treated and the severity of the disorder; activity of specific active agent employed; specific composition employed; age, body weight, general health, sex and diet of the subject; time of administration, and rate of excretion of the specific active agent employed; duration of the treatment; drugs and/or additional therapies used in combination or coincidental with specific compound(s) employed, and like factors well known in the medical arts.

The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered intraperitoneally or intravenously. Sterile injectable forms of the compositions of this invention may be aqueous or oleaginous suspension. These suspensions may be formulated according to techniques known in the art using dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

3. Description of Exemplary Embodiments 3.1 Drug Product

Some embodiments of the present invention provide methods for preparing drug product comprising SN-38, multiblock copolymer of Formula I, and iron.

One embodiment of the current invention provides a method for preparing a sterile, lyophilized drug product containing SN-38, multiblock copolymer of Formula I, and iron. This formulation would be suitable for administration to a patient. The formulation is comprised of SN-38, multiblock copolymer of Formula I, iron, and a cryoprotectant. In some embodiments, a general method for providing said formulation comprises the steps of preparing an aqueous solution of multiblock copolymer of Formula I at pH 12±0.5, adding a cryoprotectant, adjusting the pH to 6±0.1, preparing a solution of SN-38 in DMSO, adding the SN-38 solution to the solution of multiblock copolymer of Formula I and the cryoprotectant and mixing to form an emulsion, passing said emulsion through a microfluidizer, concentrating, diafiltration against an aqueous solution of a cryoprotectant, adding an iron salt, adjusting the pH to 6±0.2, sterile filtration (e.g. aseptic filtration), filling vials under sterile conditions, lyophilizing under sterile conditions, and sealing vials under sterile conditions.

Suitable cryoprotectants include, but are not limited to: sugars, monosaccharides, disaccharides, polyalcohols, mannitol, sorbitol, sucrose, trehalose, dextran, and dextrose. A preferred aspect of the present invention is the use of trehalose as the cryoprotectant.

Suitable iron salts include, but are not limited to, iron(III) fluoride, iron(III) chloride, iron(III) citrate, iron(III) bromide, iron(III) sulfate, iron(III) nitrate, iron(III) oxalate, iron(III) phosphate, iron(III) pyrophosphate, iron(II) bromide, iron(II) chloride, iron(II) fluoride, iron(II) iodide, iron(II) molybdate, iron(II) oxalate, iron(II) perchlorate, iron(II) sulfate, iron(II) tetrafluoroborate, potassium hexacyanoferrate(II), and their hydrates. A preferred aspect of the present invention is the use of iron(III) chloride as the iron salt.

As described above, herein, SN-38 is known to comprise impurities including, but not limited to, 7-ethyl camptothecin, 10-hydroxy camptothecin, and 10-hydroxy-7-methyl camptothecin.

One embodiment of the present invention provides a composition comprising SN-38, multiblock copolymer of Formula I, and iron.

One embodiment of the present invention provides a composition comprising SN-38, multiblock copolymer of Formula I, iron, and a cryoprotectant.

One embodiment of the present invention provides a composition comprising SN-38, multiblock copolymer of Formula I, iron, and a sugar.

One embodiment of the present invention provides a composition comprising SN-38, multiblock copolymer of Formula I, iron, and a monosaccharide.

One embodiment of the present invention provides a composition comprising SN-38, multiblock copolymer of Formula I, iron, and a disaccharide.

One embodiment of the present invention provides a composition comprising SN-38, multiblock copolymer of Formula I, iron, and a polyalcohol.

One embodiment of the present invention provides a composition comprising SN-38, multiblock copolymer of Formula I, iron, and mannitol.

One embodiment of the present invention provides a composition comprising SN-38, multiblock copolymer of Formula I, iron, and sorbitol.

One embodiment of the present invention provides a composition comprising SN-38, multiblock copolymer of Formula I, iron, and sucrose.

One embodiment of the present invention provides a composition comprising SN-38, multiblock copolymer of Formula I, iron, and dextran.

One embodiment of the present invention provides a composition comprising SN-38, multiblock copolymer of Formula I, iron, and dextrose.

One embodiment of the present invention provides a composition comprising SN-38, multiblock copolymer of Formula I, iron, and trehalose.

One embodiment of the present invention provides a composition comprising SN-38, multiblock copolymer of Formula I, iron, trehalose, and 7-ethyl camptothecin.

One embodiment of the present invention provides a composition comprising SN-38, multiblock copolymer of Formula I, iron, trehalose, and 10-hydroxy camptothecin.

One embodiment of the present invention provides a composition comprising SN-38, multiblock copolymer of Formula I, iron, trehalose, and 10-hydroxy-7-methyl camptothecin.

One embodiment of the present invention provides a composition comprising SN-38, multiblock copolymer of Formula I, iron, trehalose, and at least one of, or both of 7-ethyl camptothecin, and 10-hydroxy camptothecin.

One embodiment of the present invention provides a composition comprising SN-38, multiblock copolymer of Formula I, iron, trehalose, and at least one of, two of, or all three of 7-ethyl camptothecin, 10-hydroxy camptothecin, and 10-hydroxy-7-methyl camptothecin.

One embodiment of the present invention provides a composition comprising SN-38, multiblock copolymer of Formula I, iron, trehalose, and at least one of, or both of 7-ethyl camptothecin, and 10-hydroxy-7-methyl camptothecin.

One embodiment of the present invention provides a composition comprising SN-38, multiblock copolymer of Formula I, iron, trehalose, and at least one of, or both of 10-hydroxy camptothecin, and 10-hydroxy-7-methyl camptothecin.

One embodiment of the present invention provides a composition comprising SN-38, multiblock copolymer of Formula I, iron, trehalose, and 7-ethyl camptothecin,
wherein:
the 7-ethyl camptothecin is between about 0.0001 and about 0.04 weight percent of the composition.

One embodiment of the present invention provides a composition comprising SN-38, multiblock copolymer of Formula I, iron, trehalose, and 10-hydroxy camptothecin,
wherein:
the 10-hydroxy camptothecin is between about 0.00005 and about 0.02 weight percent of the composition.

One embodiment of the present invention provides a composition comprising SN-38, multiblock copolymer of Formula I, iron, trehalose, and 10-hydroxy-7-methyl camptothecin,
wherein:
the 10-hydroxy-7-methyl camptothecin is between about 0.00005 and about 0.02 weight percent of the composition.

One embodiment of the present invention provides a composition comprising SN-38, multiblock copolymer of Formula I, iron, trehalose, 7-ethyl camptothecin, 10-hydroxy camptothecin, and 10-hydroxy-7-methyl camptothecin,
wherein:
the 7-ethyl camptothecin is between about 0.0001 and about 0.04 weight percent of the composition,
10-hydroxy camptothecin is between about 0.00005 and about 0.02 weight percent of the composition,
and the 10-hydroxy-7-methyl camptothecin is between about 0.00005 and about 0.02 weight percent of the composition.

One embodiment of the present invention provides a composition comprising SN-38, multiblock copolymer of Formula I, iron, trehalose, 7-ethyl camptothecin, 10-hydroxy camptothecin, and 10-hydroxy-7-methyl camptothecin,
wherein:
the 7-ethyl camptothecin is between about 0.0001 and about 0.04 weight percent of the composition,
the 10-hydroxy camptothecin is between about 0.00005 and about 0.02 weight percent of the composition,
and the 10-hydroxy-7-methyl camptothecin is between about 0.00005 and about 0.02 weight percent of the composition.

One embodiment of the present invention provides a composition comprising SN-38, multiblock copolymer of Formula I, iron, trehalose, 7-ethyl camptothecin, and 10-hydroxy-7-methyl camptothecin,
wherein:
the 7-ethyl camptothecin is between about 0.0001 and about 0.04 weight percent of the composition,
and the 10-hydroxy-7-methyl camptothecin is between about 0.00005 and about 0.02 weight percent of the composition.

One embodiment of the present invention provides a composition comprising SN-38, multiblock copolymer of Formula I, iron, trehalose, 10-hydroxy camptothecin, and 10-hydroxy-7-methyl camptothecin,
wherein:
the 10-hydroxy camptothecin is between about 0.00005 and about 0.02 weight percent of the composition, and the 10-hydroxy-7-methyl camptothecin is between about 0.00005 and about 0.02 weight percent of the composition.

One embodiment of the present invention provides a composition comprising SN-38, multiblock copolymer of Formula I, and iron,
wherein:
the SN-38 is between about 1.60 and about 1.77 weight percentage of the composition,
the multiblock copolymer of Formula I is between about 39.9 and about 48.7 weight percentage of the composition,
and the iron is between about 1.01 and about 1.52 weight percentage of the composition.

One embodiment of the present invention provides a composition comprising SN-38, multiblock copolymer of Formula I, and iron,
wherein:
the SN-38 is between about 1.52 and about 1.86 weight percentage of the composition,
the multiblock copolymer of Formula I is between about 35.4 and about 53.2 weight percentage of the composition,
and the iron is between about 0.5 and about 4 weight percentage of the composition.

One embodiment of the present invention provides a composition comprising SN-38, multiblock copolymer of Formula I, and iron,
wherein:
the SN-38 is between about 1.35 and about 2.03 weight percentage of the composition,
the multiblock copolymer of Formula I is between about 31.0 and about 57.6 weight percentage of the composition,
and the iron is between about 0.25 and about 5.1 weight percentage of the composition.

One embodiment of the present invention provides a composition comprising SN-38, multiblock copolymer of Formula I, and iron,
wherein:
the SN-38 is between about 0.5 and about 2.5 weight percentage of the composition,
the multiblock copolymer of Formula I is between about 20 and about 60 weight percentage of the composition,
and the iron is between about 0.01 and about 5 weight percentage of the composition.

One embodiment of the present invention provides a composition comprising SN-38, multiblock copolymer of Formula I, iron, and a cryoprotectant,
wherein:
the SN-38 is between about 1.60 and about 1.77 weight percentage of the composition,
the multiblock copolymer of Formula I is between about 39.9 and about 48.7 weight percentage of the composition,
the iron is between about 1.01 and about 1.52 weight percentage of the composition,
and the cryoprotectant is between about 50.1 and about 58.0 weight percentage of the composition.

One embodiment of the present invention provides a composition comprising SN-38, multiblock copolymer of Formula I, iron, and a cryoprotectant,
wherein:
the SN-38 is between about 1.52 and about 1.86 weight percentage of the composition,
the multiblock copolymer of Formula I is between about 35.4 and about 53.2 weight percentage of the composition,
the iron is between about 0.5 and about 4 weight percentage of the composition,
and the cryoprotectant is between about 47.5 and about 68.8 weight percentage of the composition.

One embodiment of the present invention provides a composition comprising SN-38, multiblock copolymer of Formula I, iron, and a cryoprotectant,
wherein:
the SN-38 is between about 1.35 and about 2.03 weight percentage of the composition,
the multiblock copolymer of Formula I is between about 31.0 and about 57.6 weight percentage of the composition,
the iron is between about 0.25 and about 5.1 weight percentage of the composition,
and the cryoprotectant is between about 36.9 and about 79.1 weight percentage of the composition.

One embodiment of the present invention provides a composition comprising SN-38, multiblock copolymer of Formula I, iron, and a cryoprotectant,
wherein:
the SN-38 is between about 0.5 and about 2.5 weight percentage of the composition,
the multiblock copolymer of Formula I is between about 20 and about 60 weight percentage of the composition,
the iron is between about 0.01 and about 5 weight percentage of the composition,
and the cryoprotectant is between about 20 and about 80 weight percentage of the composition.

One embodiment of the present invention provides a composition comprising SN-38, multiblock copolymer of Formula I, iron, and trehalose,
wherein:
the SN-38 is between about 1.60 and about 1.77 weight percentage of the composition,
the multiblock copolymer of Formula I is between about 39.9 and about 48.7 weight percentage of the composition,
the iron is between about 1.01 and about 1.52 weight percentage of the composition,
and the trehalose is between about 50.1 and about 58.0 weight percentage of the composition.

One embodiment of the present invention provides a composition comprising SN-38, multiblock copolymer of Formula I, iron, and trehalose,
wherein:
the SN-38 is between about 1.52 and about 1.86 weight percentage of the composition,
the multiblock copolymer of Formula I is between about 35.4 and about 53.2 weight percentage of the composition,
the iron is between about 0.5 and about 4 weight percentage of the composition,
and the trehalose is between about 47.5 and about 68.6 weight percentage of the composition.

One embodiment of the present invention provides a composition comprising SN-38, multiblock copolymer of Formula I, iron, and trehalose,
wherein:
the SN-38 is between about 1.35 and about 2.03 weight percentage of the composition,
the multiblock copolymer of Formula I is between about 31.0 and about 57.6 weight percentage of the composition, the iron is between about 0.25 and about 5.1 weight percentage of the composition,
and the trehalose is between about 36.9 and about 79.1 weight percentage of the composition.

One embodiment of the present invention provides a composition comprising SN-38, multiblock copolymer of Formula I, iron, and trehalose,
wherein:
the SN-38 is between about 0.5 and about 2.5 weight percentage of the composition,
the multiblock copolymer of Formula I is between about 20 and about 60 weight percentage of the composition,
the iron is between about 0.01 and about 5 weight percentage of the composition,
and the trehalose is between about 20 and about 80 weight percentage of the composition.

One embodiment of the present invention provides a composition comprising SN-38, multiblock copolymer of Formula I, iron, trehalose, and 7-ethyl camptothecin,
wherein:
the SN-38 is between about 1.60 and about 1.77 weight percentage of the composition,
the multiblock copolymer of Formula I is between about 39.9 and about 48.7 weight percentage of the composition,
the iron is between about 1.01 and about 1.52 weight percentage of the composition,
the trehalose is between about 50.1 and about 58.0 weight percentage of the composition,
and the 7-ethyl camptothecin is between about 0.001 and about 0.04 weight percentage of the composition.

One embodiment of the present invention provides a composition comprising SN-38, multiblock copolymer of Formula I, iron, trehalose, and 7-ethyl camptothecin,
wherein:
the SN-38 is between about 1.52 and about 1.86 weight percentage of the composition,
the multiblock copolymer of Formula I is between about 35.4 and about 53.2 weight percentage of the composition,
the iron is between about 0.5 and about 4 weight percentage of the composition,
the trehalose is between about 47.5 and about 68.8 weight percentage of the composition,
and the 7-ethyl camptothecin is between about 0.0001 and about 0.04 weight percentage of the composition.

One embodiment of the present invention provides a composition comprising SN-38, multiblock copolymer of Formula I, iron, trehalose, and 7-ethyl camptothecin,
wherein:
the SN-38 is between about 1.35 and about 2.03 weight percentage of the composition,
the multiblock copolymer of Formula I is between about 31.0 and about 57.6 weight percentage of the composition,
the iron is between about 0.25 and about 5.1 weight percentage of the composition,
the trehalose is between about 36.9 and about 79.1 weight percentage of the composition,
and the 7-ethyl camptothecin is between about 0.00001 and about 0.1 weight percentage of the composition.

One embodiment of the present invention provides a composition comprising SN-38, multiblock copolymer of Formula I, iron, trehalose, and 7-ethyl camptothecin,
wherein:
the SN-38 is between about 0.5 and about 2.5 weight percentage of the composition,
the multiblock copolymer of Formula I is between about 20 and about 60 weight percentage of the composition,
the iron is between about 0.01 and about 5 weight percentage of the composition,
the trehalose is between about 20 and about 80 weight percentage of the composition,
and the 7-ethyl camptothecin is between about 0.00001 and about 0.1 weight percentage of the composition.

One embodiment of the present invention provides a composition comprising SN-38, multiblock copolymer of Formula I, iron, trehalose, 7-ethyl camptothecin, 10-hydroxy camptothecin, and 10-hydroxy-7-methyl camptothecin,
wherein:
the SN-38 is between about 1.60 and about 1.77 weight percentage of the composition,
the multiblock copolymer of Formula I is between about 39.9 and about 48.7 weight percentage of the composition,
the iron is between about 1.01 and about 1.52 weight percentage of the composition,
the trehalose is between about 50.1 and about 58.0 weight percentage of the composition,
the 7-ethyl camptothecin is between about 0.001 and about 0.04 weight percentage of the composition,
the 10-hydroxy camptothecin is between about 0.0005 and about 0.02 weight percentage of the composition,
and the 10-hydroxy-7-methyl camptothecin is between about 0.0005 and about 0.02 weight percentage of the composition.

One embodiment of the present invention provides a composition comprising SN-38, multiblock copolymer of Formula I, iron, trehalose, 7-ethyl camptothecin, 10-hydroxy camptothecin, and 10-hydroxy-7-methyl camptothecin,
wherein:
the SN-38 is between about 1.52 and about 1.86 weight percentage of the composition,
the multiblock copolymer of Formula I is between about 35.4 and about 53.2 weight percentage of the composition,
the iron is between about 0.5 and about 4 weight percentage of the composition,
the trehalose is between about 47.5 and about 68.8 weight percentage of the composition,
the 7-ethyl camptothecin is between about 0.0001 and about 0.04 weight percentage of the composition,
the 10-hydroxy camptothecin is between about 0.00005 and about 0.02 weight percentage of the composition,
and the 10-hydroxy-7-methyl camptothecin is between about 0.00005 and about 0.02 weight percentage of the composition.

One embodiment of the present invention provides a composition comprising SN-38, multiblock copolymer of Formula I, iron, trehalose, 7-ethyl camptothecin, 10-hydroxy camptothecin, and 10-hydroxy-7-methyl camptothecin,
wherein:
the SN-38 is between about 1.35 and about 2.03 weight percentage of the composition,
the multiblock copolymer of Formula I is between about 31.0 and about 57.6 weight percentage of the composition,
the iron is between about 0.25 and about 5.1 weight percentage of the composition,
the trehalose is between about 36.9 and about 79.1 weight percentage of the composition, the 7-ethyl camptothecin is between about 0.00001 and about 0.1 weight percentage of the composition,
the 10-hydroxy camptothecin is between about 0.000005 and about 0.05 weight percentage of the composition,
and the 10-hydroxy-7-methyl camptothecin is between about 0.000005 and about 0.05 weight percentage of the composition.

One embodiment of the present invention provides a composition comprising SN-38, multiblock copolymer of Formula I, iron, trehalose, 7-ethyl camptothecin, 10-hydroxy camptothecin, and 10-hydroxy-7-methyl camptothecin,
wherein:
the SN-38 is between about 0.5 and about 2.5 weight percentage of the composition,
the multiblock copolymer of Formula I is between about 20 and about 60 weight percentage of the composition,
the iron is between about 0.01 and about 5 weight percentage of the composition,
the trehalose is between about 20 and about 80 weight percentage of the composition,
the 7-ethyl camptothecin is between about 0.00001 and about 0.1 weight percentage of the composition,
the 10-hydroxy camptothecin is between about 0.000005 and about 0.05 weight percentage of the composition,
and the 10-hydroxy-7-methyl camptothecin is between about 0.000005 and about 0.05 weight percentage of the composition.

One embodiment of the present invention provides a composition comprising SN-38, multiblock copolymer of Formula I, iron, trehalose, and 7-ethyl camptothecin,
wherein:
the SN-38 is between about 0.5 and about 2.5 weight percentage of the composition,
the multiblock copolymer of Formula I is between about 20 and about 60 weight percentage of the composition,
the iron is between about 0.01 and about 5 weight percentage of the composition,
the trehalose is between about 20 and about 80 weight percentage of the composition,
and the 7-ethyl camptothecin is between about 0.00001 and about 0.1 weight percentage of the composition.

One embodiment of the present invention provides a composition comprising SN-38, multiblock copolymer of Formula I, iron, trehalose, and 10-hydroxy camptothecin,
wherein:
the SN-38 is between about 0.5 and about 2.5 weight percentage of the composition,
the multiblock copolymer of Formula I is between about 20 and about 60 weight percentage of the composition,
the iron is between about 0.01 and about 5 weight percentage of the composition,
the trehalose is between about 20 and about 80 weight percentage of the composition,
and the 10-hydroxy camptothecin is between about 0.000005 and about 0.05 weight percentage of the composition.

One embodiment of the present invention provides a composition comprising SN-38, multiblock copolymer of Formula I, iron, trehalose, and 10-hydroxy-7-methyl camptothecin,
wherein:
the SN-38 is between about 0.5 and about 2.5 weight percentage of the composition,
the multiblock copolymer of Formula I is between about 20 and about 60 weight percentage of the composition,
the iron is between about 0.01 and about 5 weight percentage of the composition,
the trehalose is between about 20 and about 80 weight percentage of the composition,
and the 10-hydroxy-7-methyl camptothecin is between about 0.000005 and about 0.05 weight percentage of the composition.

One embodiment of the present invention provides a composition comprising SN-38, multiblock copolymer of Formula I, iron, trehalose, 10-hydroxy camptothecin, and 10-hydroxy-7-methyl camptothecin,
wherein:
the SN-38 is between about 0.5 and about 2.5 weight percentage of the composition,
the multiblock copolymer of Formula I is between about 20 and about 60 weight percentage of the composition,
the iron is between about 0.01 and about 5 weight percentage of the composition,
the trehalose is between about 20 and about 80 weight percentage of the composition,
the 10-hydroxy camptothecin is between about 0.000005 and about 0.05 weight percentage of the composition,
and the 10-hydroxy-7-methyl camptothecin is between about 0.000005 and about 0.05 weight percentage of the composition.

One embodiment of the present invention provides a composition comprising SN-38, multiblock copolymer of Formula I, iron, trehalose, 7-ethyl camptothecin, and 10-hydroxy-7-methyl camptothecin,
wherein:
the SN-38 is between about 0.5 and about 2.5 weight percentage of the composition,
the multiblock copolymer of Formula I is between about 20 and about 60 weight percentage of the composition,
the iron is between about 0.01 and about 5 weight percentage of the composition,
the trehalose is between about 20 and about 80 weight percentage of the composition,
the 7-ethyl camptothecin is between about 0.00001 and about 0.1 weight percentage of the composition,
and the 10-hydroxy-7-methyl camptothecin is between about 0.000005 and about 0.05 weight percentage of the composition.

One embodiment of the present invention provides a composition comprising SN-38, multiblock copolymer of Formula I, iron, trehalose, 10-hydroxy camptothecin, and 10-hydroxy-7-methyl camptothecin,
wherein:
the SN-38 is between about 0.5 and about 2.5 weight percentage of the composition,
the multiblock copolymer of Formula I is between about 20 and about 60 weight percentage of the composition,
the iron is between about 0.01 and about 5 weight percentage of the composition,
the trehalose is between about 20 and about 80 weight percentage of the composition,
the 10-hydroxy camptothecin is between about 0.000005 and about 0.05 weight percentage of the composition,
and the 10-hydroxy-7-methyl camptothecin is between about 0.000005 and about 0.05 weight percentage of the composition.

In some embodiments, the present invention provides a composition comprising
from about 14.4 mg to about 17.6 mg of SN-38,
from about 336 mg to about 504 mg of the multiblock copolymer of Formula I,
and from about 4.74 mg to about 37.9 mg of iron.

In some embodiments, the present invention provides a composition comprising
from about 14.4 mg to about 17.6 mg of SN-38,
from about 336 mg to about 504 mg of the multiblock copolymer of Formula I,
from about 4.74 mg to about 37.9 mg of iron,
and from about 450 to about 650 mg of trehalose.

In some embodiments, the present invention provides a composition comprising
from about 14.4 mg to about 17.6 mg of SN-38,
from about 336 mg to about 504 mg of the multiblock copolymer of Formula I,
from about 4.74 mg to about 37.9 mg of iron,
from about 450 to about 650 mg of trehalose,
and from about 0.001 mg to about 0.4 mg of 7-ethyl camptothecin.

In some embodiments, the present invention provides a composition comprising
from about 14.4 mg to about 17.6 mg of SN-38,
from about 336 mg to about 504 mg of the multiblock copolymer of Formula I,
from about 4.74 mg to about 37.9 mg of iron,
from about 450 to about 650 mg of trehalose,
and from about 0.0005 mg to about 0.2 mg of 10-hydroxy camptothecin.

In some embodiments, the present invention provides a composition comprising
from about 14.4 mg to about 17.6 mg of SN-38,
from about 336 mg to about 504 mg of the multiblock copolymer of Formula I,
from about 4.74 mg to about 37.9 mg of iron,
from about 450 to about 650 mg of trehalose,
and from about 0.0005 mg to about 0.2 mg of 10-hydroxy-7-methyl-camptothecin.

In some embodiments, the present invention provides a composition comprising
from about 14.4 mg to about 17.6 mg of SN-38,
from about 336 mg to about 504 mg of the multiblock copolymer of Formula I,
from about 4.74 mg to about 37.9 mg of iron,
from about 450 to about 650 mg of trehalose,
from about 0.001 mg to about 0.4 mg of 7-ethyl camptothecin,
and from about 0.0005 mg to about 0.2 mg of 10-hydroxy camptothecin.

In some embodiments, the present invention provides a composition comprising
from about 14.4 mg to about 17.6 mg of SN-38,
from about 336 mg to about 504 mg of the multiblock copolymer of Formula I,
from about 4.74 mg to about 37.9 mg of iron,
from about 450 to about 650 mg of trehalose,
from about 0.001 mg to about 0.4 mg of 7-ethyl camptothecin,
and from about 0.0005 mg to about 0.2 mg of 10-hydroxy-7-methyl camptothecin.

In some embodiments, the present invention provides a composition comprising
from about 14.4 mg to about 17.6 mg of SN-38,
from about 336 mg to about 504 mg of the multiblock copolymer of Formula I,
from about 4.74 mg to about 37.9 mg of iron,
from about 450 to about 650 mg of trehalose,
from about 0.0005 mg to about 0.2 mg of 10-hydroxy camptothecin,
and from about 0.0005 mg to about 0.2 mg of 10-hydroxy-7-methyl camptothecin.

In some embodiments, the present invention provides a composition comprising
from about 14.4 mg to about 17.6 mg of SN-38,
from about 336 mg to about 504 mg of the multiblock copolymer of Formula I,
from about 4.74 mg to about 37.9 mg of iron,
from about 450 to about 650 mg of trehalose,
from about 0.001 mg to about 0.4 mg of 7-ethyl camptothecin,
from about 0.0005 mg to about 0.2 mg of 10-hydroxy camptothecin,
and from about 0.0005 mg to about 0.2 mg of 10-hydroxy-7-methyl camptothecin.

In some embodiments, the present invention provides a composition comprising
about 16 mg of SN-38,
about 420 mg of the multiblock copolymer of Formula I,
and about 12 mg of iron.

In some embodiments, the present invention provides a composition comprising
about 16 mg of SN-38,
about 420 mg of the multiblock copolymer of Formula I,
about 12 mg of iron,
and about 500 mg of trehalose.

3.2 Methods of Treatment

As described generally above, the present invention provides compositions comprising SN-38. As such, in some embodiments, the present invention provides a method for the treating a disease, disorder, or condition treatable by SN-38, such as proliferation diseases such as cancer.

In some embodiments, the present invention provides a method for treating a cancer selected from pancreatic, lung, gastroesophageal, colorectal cancer, gastrointestinal, or breast, in a patient in need thereof, comprising administering to the patient a provided composition.

In some embodiments, the present invention provides a method of treating a cancer. For instance, in some embodiments, the present invention provides a method for treating cancer in a patient comprising the step of administering to said patient a composition comprising SN-38, a multiblock copolymer and iron. In some embodiments, the cancer is recurring. In certain embodiments, the cancer is refractory. In some embodiments, the cancer is metastatic. In some embodiments, the cancer is locally advanced In some embodiments, the cancer is selected from multiple myeloma, breast, ovary, cervix, prostate, testis, genitourinary tract, esophagus, larynx, glioblastoma, neuroblastoma, stomach (gastric), skin, keratoacanthoma, lung, epidermoid carcinoma, large cell carcinoma, small cell carcinoma, lung, bone, colon, thyroid, adenoma, pancreas, adenocarcinoma, thyroid, follicular carcinoma, undifferentiated carcinoma, papillary carcinoma, seminoma, melanoma (including uveal melanoma) sarcoma, bladder carcinoma, liver carcinoma (e.g., hepatocellular carcinoma (HCC)) and biliary passages, kidney carcinoma, myeloid disorders, lymphoid disorders, Hodgkin's, hairy cells, buccal cavity and pharynx (oral), lip, tongue, mouth, pharynx, small intestine, colorectal carcinoma, large intestine, rectum, brain and central nervous system, endometrial, multiple myeloma (MM), prostate, AML, and leukemia.

In some embodiments, the cancer is selected from carcinoma, lymphoma, blastoma, sarcoma, and leukemia. In some embodiments, a sarcoma is a soft tissue sarcoma. In some embodiments, a lymphoma is non-hodgkins lymphoma. In some embodiments, a lymphoma is large cell immunoblastic lymphoma. In some embodiments, the cancer is selected from adenocarcinoma; adenoma; adrenocortical cancer; bladder cancer; bone cancer; brain cancer; breast cancer; cancer of the buccal cavity; cervical cancer; colon cancer; colorectal cancer; endometrial or uterine carcmoma; epidermoid carcinoma; esophageal cancer; eye cancer; follicular carcmoma; gallbladder cancer; prostate, AML, multiple myeloma (MM), gastrointestinal cancer, such as, for example, gastrointestinal stromal tumor; cancer of the genitourinary tract; glioblastoma; hairy cell carcinoma; various types of head and neck cancer; hepatic carcinoma; hepatocellular cancer; Hodgkin's disease; keratoacanthoma; kidney cancer; large cell carcinoma; cancer of the large intestine; laryngeal cancer; liver cancer; lung cancer, such as, for example, adenocarcinoma of the lung, anaplastic carcinoma of the lung, papillary lung adenocarcinoma, small-cell lung cancer, squamous carcinoma of the lung, non-small cell lung cancer; melanoma and nonmelanoma skin cancer; lymphoid disorders; myeloproliferative disorders, such as, for example, polycythemia vera, essential thrombocythemia, chronic idiopathic myelofibrosis, myeloid metaplasia with myelofibrosis, chronic myeloid leukemia (CML), chronic myelomonocytic leukemia, chronic eosinophilic leukemia, chronic lymphocytic leukemia (CLL), hypereosinophilic syndrome, systematic mast cell disease, atypical CML, AML, or juvenile myelomonocytic leukemia; plasmacytoma; multiple myeloma; neuroblastoma; ovarian cancer; papillary carcinoma; pancreatic cancer; cancer of the peritoneum; prostate cancer, including benign prostatic hyperplasia; rectal cancer; salivary gland carcinoma; sarcoma; seminoma; squamous cell cancer; small cell carcinoma; cancer of the small intestine; stomach cancer; testicular cancer; thyroid cancer; undifferentiated carcinoma; and vulval cancer.

In certain embodiments, the cancer is selected from melanoma, pancreatic cancer, thyroid cancer, colorectal cancer, lung cancer (e.g., non-small cell lung cancer), breast cancer, endometrial cancer, prostate cancer, ovarian cancer, hepatocellular carcinoma (HCC), multiple myeloma (MM), and leukemia. In some embodiments, a leukemia is an acute leukemia. In certain embodiments, a leukemia is acute myeloid leukemia. In certain embodiments, a leukemia is acute lymphoblastic leukemia.

In some embodiments, the cancer is selected from pancreatic, lung, gastroesophageal, colorectal cancer, gastrointestinal, or breast.

In some embodiments, the cancer is melanoma. In certain embodiments, the melanoma is uveal melanoma. In some embodiments, the melanoma is a melanoma of the skin. In certain embodiments, the melanoma is locally advanced. In some embodiments, the melanoma is metastatic. In some embodiments, the melanoma is recurring. In some embodiments, the melanoma is refractory.

In some embodiments, the cancer is colorectal cancer. In certain embodiments, the colorectal cancer is locally advanced. In certain embodiments, the colorectal cancer is metastatic. In certain embodiments, the colorectal cancer is recurring. In certain embodiments, the colorectal cancer is refractory.

In some embodiments, the cancer is pancreatic cancer. In certain embodiments, the pancreatic cancer is locally advanced. In certain embodiments, the pancreatic cancer is metastatic. In certain embodiments, the pancreatic cancer is locally recurring. In certain embodiments, the pancreatic cancer is refractory. In certain embodiments, the pancreatic cancer is a pancreatic ductal adenocarcinoma (PDAC).

In some embodiments, the cancer is a papillary thyroid cancer. In certain embodiments, the papillary thyroid cancer is locally advanced. In some embodiments, the papillary thyroid cancer is metastatic. In certain embodiments, the papillary thyroid cancer is refractory. In some embodiments, the papillary thyroid cancer is recurring.

In some embodiments, the cancer is lung cancer. In certain embodiments, the lung cancer is non-small cell lung cancer (NSCLC). In certain embodiments, the lung cancer is locally advanced. In certain embodiments, the lung cancer is metastatic. In certain embodiments, the lung cancer is recurring.

In certain embodiments, the cancer is a leukemia. In some embodiments, a leukemia is a chronic leukemia. In certain embodiments, a leukemia is chronic myeloid leukemia. In some embodiments, a leukemia is an acute leukemia. In certain embodiments, a leukemia is acute myeloid leukemia (AML). In certain embodiments, a leukemia is acute monocytic leukemia (AMoL, or AML-M5). In certain embodiments, a leukemia is acute lymphoblastic leukemia (ALL). In certain embodiments, a leukemia is acute T cell leukemia. In certain embodiments, a leukemia is myelomonoblastic leukemia. In certain embodiments, a leukemia is human B cell precursor leukemia. In certain embodiments, a leukemia has a Flt3 mutation or rearrangement.

In some embodiments, the cancer is a CNS cancer, for instance CNS tumors. In certain embodiments, a CNS tumor is a glioblastoma or glioblastoma multiforme (GBM). In some embodiments, the present invention provides a method of treating stomach (gastric) and esophageal tumors and cancers.

In some embodiments, the cancer is multiple myeloma (MM). In certain embodiments, the multiple myeloma is locally advanced. In certain embodiments, the multiple myeloma is metastatic. In certain embodiments, the multiple myeloma is locally recurring. In certain embodiments, the multiple myeloma is refractory.

In some embodiments, the cancer is hepatocellular carcinoma (HCC). In certain embodiments, the HCC is locally advanced. In certain embodiments, the HCC is metastatic. In certain embodiments, the HCC is locally recurring. In certain embodiments, the HCC is refractory.

In some embodiments, the cancer is selected from breast, colorectal, endometrial, hematological, leukemia (e.g., AML), liver, lung, melanoma, ovarian, prostate, or thyroid.

In some embodiments, the cancer is selected from breast, colorectal, endometrial, liver, lung, melanoma, ovarian, pancreatic, or thyroid.

In some embodiments, the cancer is selected from colorectal, lung, melanoma, or pancreatic.

In some embodiments, the cancer is selected from colorectal, melanoma, or pancreatic.

3.3. Dosing

One embodiment of the present invention provides methods for treating, stabilizing, or lessening the severity or progression of one or more proliferation diseases (e.g. cancer), wherein the method comprises administering to a patient in need thereof a provided pharmaceutically acceptable composition comprising SN-38, multiblock copolymer of Formula I, and iron, as described herein.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, and a cryoprotectant.

One embodiment of the present invention provides methods for treating, stabilizing, or lessening the severity or progression of one or more proliferation diseases (e.g.

cancer), wherein the method comprises administering to a patient in need thereof a pharmaceutically acceptable composition comprising SN-38, multiblock copolymer of Formula I, iron, and a sugar.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, and a monosaccharide.

The present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, and a disaccharide.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, and a polyalcohol.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, and mannitol.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, and sorbitol.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, and sucrose.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, and dextran.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, and dextrose.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, and trehalose.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, trehalose, and 7-ethyl camptothecin.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, trehalose, and 10-hydroxy camptothecin.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, trehalose, and 10-hydroxy-7-methyl camptothecin.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, trehalose, and at least one of, or both of 7-ethyl camptothecin, and 10-hydroxy camptothecin.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, trehalose, and at least one of, two of, or all three of 7-ethyl camptothecin, 10-hydroxy camptothecin, and 10-hydroxy-7-methyl camptothecin.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, trehalose, and at least one of, or both of 7-ethyl camptothecin, and 10-hydroxy-7-methyl camptothecin.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, trehalose, and at least one of, or both of 10-hydroxy camptothecin, and 10-hydroxy-7-methyl camptothecin.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, trehalose, and 7-ethyl camptothecin,
wherein:
the 7-ethyl camptothecin is between about 0.0001 and about 0.04 weight percent of the composition.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, trehalose, and 10-hydroxy camptothecin,
wherein:
the 10-hydroxy camptothecin is between about 0.00005 and about 0.02 weight percent of the composition.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, trehalose, and 10-hydroxy-7-methyl camptothecin,
wherein:
the 10-hydroxy-7-methyl camptothecin is between about 0.00005 and about 0.02 weight percent of the composition.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, trehalose, 7-ethyl camptothecin, 10-hydroxy camptothecin, and 10-hydroxy-7-methyl camptothecin,
wherein:
the 7-ethyl camptothecin is between about 0.0001 and about 0.04 weight percent of the composition,
10-hydroxy camptothecin is between about 0.00005 and about 0.02 weight percent of the composition,
and the 10-hydroxy-7-methyl camptothecin is between about 0.00005 and about 0.02 weight percent of the composition.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, trehalose, 7-ethyl camptothecin, 10-hydroxy camptothecin, and 10-hydroxy-7-methyl camptothecin,
wherein:
the 7-ethyl camptothecin is between about 0.0001 and about 0.04 weight percent of the composition,
the 10-hydroxy camptothecin is between about 0.00005 and about 0.02 weight percent of the composition,
and the 10-hydroxy-7-methyl camptothecin is between about 0.00005 and about 0.02 weight percent of the composition.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, trehalose, 7-ethyl camptothecin, and 10-hydroxy-7-methyl camptothecin,
wherein:
the 7-ethyl camptothecin is between about 0.0001 and about 0.04 weight percent of the composition,
and the 10-hydroxy-7-methyl camptothecin is between about 0.00005 and about 0.02 weight percent of the composition.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, trehalose, 10-hydroxy camptothecin, and 10-hydroxy-7-methyl camptothecin,
wherein:
the 10-hydroxy camptothecin is between about 0.00005 and about 0.02 weight percent of the composition,
and the 10-hydroxy-7-methyl camptothecin is between about 0.00005 and about 0.02 weight percent of the composition.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, and iron,
wherein:
the SN-38 is between about 1.60 and about 1.77 weight percentage of the composition,
the multiblock copolymer of Formula I is between about 39.9 and about 48.7 weight percentage of the composition,
and the iron is between about 1.01 and about 1.52 weight percentage of the composition.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, and iron,
wherein:
the SN-38 is between about 1.52 and about 1.86 weight percentage of the composition,
the multiblock copolymer of Formula I is between about 35.4 and about 53.2 weight percentage of the composition,
and the iron is between about 0.5 and about 4 weight percentage of the composition.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, and iron,
wherein:
the SN-38 is between about 1.35 and about 2.03 weight percentage of the composition,
the multiblock copolymer of Formula I is between about 31.0 and about 57.6 weight percentage of the composition,
and the iron is between about 0.25 and about 5.1 weight percentage of the composition.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, and iron,
wherein:
the SN-38 is between about 0.5 and about 2.5 weight percentage of the composition,
the multiblock copolymer of Formula I is between about 20 and about 60 weight percentage of the composition,
and the iron is between about 0.01 and about 5 weight percentage of the composition.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, and a cryoprotectant,
wherein:
the SN-38 is between about 1.60 and about 1.77 weight percentage of the composition,
the multiblock copolymer of Formula I is between about 39.9 and about 48.7 weight percentage of the composition,
the iron is between about 1.01 and about 1.52 weight percentage of the composition,
and the cryoprotectant is between about 50.1 and about 58.0 weight percentage of the composition.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, and a cryoprotectant,
wherein:
the SN-38 is between about 1.52 and about 1.86 weight percentage of the composition,
the multiblock copolymer of Formula I is between about 35.4 and about 53.2 weight percentage of the composition,
the iron is between about 0.5 and about 4 weight percentage of the composition,
and the cryoprotectant is between about 47.5 and about 68.8 weight percentage of the composition.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, and a cryoprotectant,
wherein:
the SN-38 is between about 1.35 and about 2.03 weight percentage of the composition,
the multiblock copolymer of Formula I is between about 31.0 and about 57.6 weight percentage of the composition,
the iron is between about 0.25 and about 5.1 weight percentage of the composition,
and the cryoprotectant is between about 36.9 and about 79.1 weight percentage of the composition.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, and a cryoprotectant,
wherein:
the SN-38 is between about 0.5 and about 2.5 weight percentage of the composition,
the multiblock copolymer of Formula I is between about 20 and about 60 weight percentage of the composition,
the iron is between about 0.01 and about 5 weight percentage of the composition,
and the cryoprotectant is between about 20 and about 80 weight percentage of the composition.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, and trehalose,
wherein:
the SN-38 is between about 1.60 and about 1.77 weight percentage of the composition,
the multiblock copolymer of Formula I is between about 39.9 and about 48.7 weight percentage of the composition,
the iron is between about 1.01 and about 1.52 weight percentage of the composition,
and the trehalose is between about 50.1 and about 58.0 weight percentage of the composition.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, and trehalose,
wherein:
the SN-38 is between about 1.52 and about 1.86 weight percentage of the composition,
the multiblock copolymer of Formula I is between about 35.4 and about 53.2 weight percentage of the composition,
the iron is between about 0.5 and about 4 weight percentage of the composition,
and the trehalose is between about 47.5 and about 68.6 weight percentage of the composition.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, and trehalose,
wherein:
the SN-38 is between about 1.35 and about 2.03 weight percentage of the composition,
the multiblock copolymer of Formula I is between about 31.0 and about 57.6 weight percentage of the composition,
the iron is between about 0.25 and about 5.1 weight percentage of the composition,
and the trehalose is between about 36.9 and about 79.1 weight percentage of the composition.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, and trehalose,
wherein:
the SN-38 is between about 0.5 and about 2.5 weight percentage of the composition,
the multiblock copolymer of Formula I is between about 20 and about 60 weight percentage of the composition,
the iron is between about 0.01 and about 5 weight percentage of the composition,
and the trehalose is between about 20 and about 80 weight percentage of the composition.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, trehalose, and 7-ethyl camptothecin,
wherein:
the SN-38 is between about 1.60 and about 1.77 weight percentage of the composition,
the multiblock copolymer of Formula I is between about 39.9 and about 48.7 weight percentage of the composition,
the iron is between about 1.01 and about 1.52 weight percentage of the composition,
the trehalose is between about 50.1 and about 58.0 weight percentage of the composition,
and the 7-ethyl camptothecin is between about 0.001 and about 0.04 weight percentage of the composition.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, trehalose, and 7-ethyl camptothecin,
wherein:
the SN-38 is between about 1.52 and about 1.86 weight percentage of the composition,
the multiblock copolymer of Formula I is between about 35.4 and about 53.2 weight percentage of the composition,
the iron is between about 0.5 and about 4 weight percentage of the composition,
the trehalose is between about 47.5 and about 68.8 weight percentage of the composition,
and the 7-ethyl camptothecin is between about 0.0001 and about 0.04 weight percentage of the composition.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, trehalose, and 7-ethyl camptothecin,
wherein:
the SN-38 is between about 1.35 and about 2.03 weight percentage of the composition,
the multiblock copolymer of Formula I is between about 31.0 and about 57.6 weight percentage of the composition,
the iron is between about 0.25 and about 5.1 weight percentage of the composition,
the trehalose is between about 36.9 and about 79.1 weight percentage of the composition,
and the 7-ethyl camptothecin is between about 0.00001 and about 0.1 weight percentage of the composition.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, trehalose, and 7-ethyl camptothecin,
wherein:
the SN-38 is between about 0.5 and about 2.5 weight percentage of the composition,
the multiblock copolymer of Formula I is between about 20 and about 60 weight percentage of the composition,
the iron is between about 0.01 and about 5 weight percentage of the composition,
the trehalose is between about 20 and about 80 weight percentage of the composition,
and the 7-ethyl camptothecin is between about 0.00001 and about 0.1 weight percentage of the composition.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, trehalose, 7-ethyl camptothecin, 10-hydroxy camptothecin, and 10-hydroxy-7-methyl camptothecin,
wherein:
the SN-38 is between about 1.60 and about 1.77 weight percentage of the composition,
the multiblock copolymer of Formula I is between about 39.9 and about 48.7 weight percentage of the composition,
the iron is between about 1.01 and about 1.52 weight percentage of the composition,
the trehalose is between about 50.1 and about 58.0 weight percentage of the composition,
the 7-ethyl camptothecin is between about 0.001 and about 0.04 weight percentage of the composition,
the 10-hydroxy camptothecin is between about 0.0005 and about 0.02 weight percentage of the composition,
and the 10-hydroxy-7-methyl camptothecin is between about 0.0005 and about 0.02 weight percentage of the composition.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, trehalose, 7-ethyl camptothecin, 10-hydroxy camptothecin, and 10-hydroxy-7-methyl camptothecin,
wherein:
the SN-38 is between about 1.52 and about 1.86 weight percentage of the composition,
the multiblock copolymer of Formula I is between about 35.4 and about 53.2 weight percentage of the composition,
the iron is between about 0.5 and about 4 weight percentage of the composition,
the trehalose is between about 47.5 and about 68.8 weight percentage of the composition,
the 7-ethyl camptothecin is between about 0.0001 and about 0.04 weight percentage of the composition,
the 10-hydroxy camptothecin is between about 0.00005 and about 0.02 weight percentage of the composition, and the 10-hydroxy-7-methyl camptothecin is between about 0.00005 and about 0.02 weight percentage of the composition.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, trehalose, 7-ethyl camptothecin, 10-hydroxy camptothecin, and 10-hydroxy-7-methyl camptothecin,
wherein:
the SN-38 is between about 1.35 and about 2.03 weight percentage of the composition,
the multiblock copolymer of Formula I is between about 31.0 and about 57.6 weight percentage of the composition,
the iron is between about 0.25 and about 5.1 weight percentage of the composition,
the trehalose is between about 36.9 and about 79.1 weight percentage of the composition,
the 7-ethyl camptothecin is between about 0.00001 and about 0.1 weight percentage of the composition,
the 10-hydroxy camptothecin is between about 0.000005 and about 0.05 weight percentage of the composition,
and the 10-hydroxy-7-methyl camptothecin is between about 0.000005 and about 0.05 weight percentage of the composition.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, trehalose, 7-ethyl camptothecin, 10-hydroxy camptothecin, and 10-hydroxy-7-methyl camptothecin,
wherein:
the SN-38 is between about 0.5 and about 2.5 weight percentage of the composition,
the multiblock copolymer of Formula I is between about 20 and about 60 weight percentage of the composition,
the iron is between about 0.01 and about 5 weight percentage of the composition,
the trehalose is between about 20 and about 80 weight percentage of the composition,
the 7-ethyl camptothecin is between about 0.00001 and about 0.1 weight percentage of the composition,
the 10-hydroxy camptothecin is between about 0.000005 and about 0.05 weight percentage of the composition,
and the 10-hydroxy-7-methyl camptothecin is between about 0.000005 and about 0.05 weight percentage of the composition.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, trehalose, and 7-ethyl camptothecin,
wherein:
the SN-38 is between about 0.5 and about 2.5 weight percentage of the composition,
the multiblock copolymer of Formula I is between about 20 and about 60 weight percentage of the composition,
the iron is between about 0.01 and about 5 weight percentage of the composition,
the trehalose is between about 20 and about 80 weight percentage of the composition,
and the 7-ethyl camptothecin is between about 0.00001 and about 0.1 weight percentage of the composition.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, trehalose, and 10-hydroxy camptothecin,
wherein:
the SN-38 is between about 0.5 and about 2.5 weight percentage of the composition,
the multiblock copolymer of Formula I is between about 20 and about 60 weight percentage of the composition,
the iron is between about 0.01 and about 5 weight percentage of the composition,
the trehalose is between about 20 and about 80 weight percentage of the composition,
and the 10-hydroxy camptothecin is between about 0.000005 and about 0.05 weight percentage of the composition.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, trehalose, and 10-hydroxy-7-methyl camptothecin,
wherein:
the SN-38 is between about 0.5 and about 2.5 weight percentage of the composition,
the multiblock copolymer of Formula I is between about 20 and about 60 weight percentage of the composition,
the iron is between about 0.01 and about 5 weight percentage of the composition,
the trehalose is between about 20 and about 80 weight percentage of the composition,
and the 10-hydroxy-7-methyl camptothecin is between about 0.000005 and about 0.05 weight percentage of the composition.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, trehalose, 10-hydroxy camptothecin, and 10-hydroxy-7-methyl camptothecin,
wherein:
the SN-38 is between about 0.5 and about 2.5 weight percentage of the composition,
the multiblock copolymer of Formula I is between about 20 and about 60 weight percentage of the composition,
the iron is between about 0.01 and about 5 weight percentage of the composition,
the trehalose is between about 20 and about 80 weight percentage of the composition,
the 10-hydroxy camptothecin is between about 0.000005 and about 0.05 weight percentage of the composition,
and the 10-hydroxy-7-methyl camptothecin is between about 0.000005 and about 0.05 weight percentage of the composition.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, trehalose, 7-ethyl camptothecin, and 10-hydroxy-7-methyl camptothecin,
wherein:
the SN-38 is between about 0.5 and about 2.5 weight percentage of the composition,
the multiblock copolymer of Formula I is between about 20 and about 60 weight percentage of the composition,
the iron is between about 0.01 and about 5 weight percentage of the composition,
the trehalose is between about 20 and about 80 weight percentage of the composition,
the 7-ethyl camptothecin is between about 0.00001 and about 0.1 weight percentage of the composition,
and the 10-hydroxy-7-methyl camptothecin is between about 0.000005 and about 0.05 weight percentage of the composition.

One embodiment of the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, iron, trehalose, 10-hydroxy camptothecin, and 10-hydroxy-7-methyl camptothecin,
wherein:
the SN-38 is between about 0.5 and about 2.5 weight percentage of the composition,
the multiblock copolymer of Formula I is between about 20 and about 60 weight percentage of the composition,
the iron is between about 0.01 and about 5 weight percentage of the composition,
the trehalose is between about 20 and about 80 weight percentage of the composition,
the 10-hydroxy camptothecin is between about 0.000005 and about 0.05 weight percentage of the composition,
and the 10-hydroxy-7-methyl camptothecin is between about 0.000005 and about 0.05 weight percentage of the composition.

In some embodiments, the present invention provides methods for treating, stabilizing, or lessening the severity or progression of one or more proliferation diseases (e.g. cancer), wherein the method comprises administering to a patient in need thereof a pharmaceutically acceptable composition comprising
from about 14.4 mg to about 17.6 mg of SN-38,
from about 336 mg to about 504 mg of the multiblock copolymer of Formula I,
and from about 4.74 mg to about 37.9 mg of iron.

In some embodiments, the present invention provides methods for treating, stabilizing, or lessening the severity or progression of one or more proliferation diseases (e.g. cancer), wherein the method comprises administering to a patient in need thereof a pharmaceutically acceptable composition comprising
from about 14.4 mg to about 17.6 mg of SN-38,
from about 336 mg to about 504 mg of the multiblock copolymer of Formula I,
from about 4.74 mg to about 37.9 mg of iron,
and from about 450 to about 650 mg of trehalose.

In some embodiments, the present invention provides methods for treating, stabilizing, or lessening the severity or progression of one or more proliferation diseases (e.g. cancer), wherein the method comprises administering to a patient in need thereof a pharmaceutically acceptable composition comprising
from about 14.4 mg to about 17.6 mg of SN-38,
from about 336 mg to about 504 mg of the multiblock copolymer of Formula I,
from about 4.74 mg to about 37.9 mg of iron,
from about 450 to about 650 mg of trehalose,
and from about 0.001 mg to about 0.4 mg of 7-ethyl camptothecin.

In some embodiments, the present invention provides methods for treating, stabilizing, or lessening the severity or progression of one or more proliferation diseases (e.g. cancer), wherein the method comprises administering to a patient in need thereof a pharmaceutically acceptable composition comprising
from about 14.4 mg to about 17.6 mg of SN-38,
from about 336 mg to about 504 mg of the multiblock copolymer of Formula I,
from about 4.74 mg to about 37.9 mg of iron,
from about 450 to about 650 mg of trehalose,
and from about 0.0005 mg to about 0.2 mg of 10-hydroxy camptothecin.

In some embodiments, the present invention provides methods for treating, stabilizing, or lessening the severity or progression of one or more proliferation diseases (e.g. cancer), wherein the method comprises administering to a patient in need thereof a pharmaceutically acceptable composition comprising
from about 14.4 mg to about 17.6 mg of SN-38,
from about 336 mg to about 504 mg of the multiblock copolymer of Formula I,
from about 4.74 mg to about 37.9 mg of iron,
from about 450 to about 650 mg of trehalose,
and from about 0.0005 mg to about 0.2 mg of 10-hydroxy-7-methyl-camptothecin.

In some embodiments, the present invention provides methods for treating, stabilizing, or lessening the severity or progression of one or more proliferation diseases (e.g. cancer), wherein the method comprises administering to a patient in need thereof a pharmaceutically acceptable composition comprising
from about 14.4 mg to about 17.6 mg of SN-38,
from about 336 mg to about 504 mg of the multiblock copolymer of Formula I,
from about 4.74 mg to about 37.9 mg of iron,
from about 450 to about 650 mg of trehalose,
from about 0.001 mg to about 0.4 mg of 7-ethyl camptothecin,
and from about 0.0005 mg to about 0.2 mg of 10-hydroxy camptothecin.

In some embodiments, the present invention provides methods for treating, stabilizing, or lessening the severity or progression of one or more proliferation diseases (e.g. cancer), wherein the method comprises administering to a patient in need thereof a pharmaceutically acceptable composition comprising
from about 14.4 mg to about 17.6 mg of SN-38,
from about 336 mg to about 504 mg of the multiblock copolymer of Formula I,
from about 4.74 mg to about 37.9 mg of iron,
from about 450 to about 650 mg of trehalose,
from about 0.001 mg to about 0.4 mg of 7-ethyl camptothecin,
and from about 0.0005 mg to about 0.2 mg of 10-hydroxy-7-methyl camptothecin.

In some embodiments, the present invention provides methods for treating, stabilizing, or lessening the severity or progression of one or more proliferation diseases (e.g. cancer), wherein the method comprises administering to a patient in need thereof a pharmaceutically acceptable composition comprising
from about 14.4 mg to about 17.6 mg of SN-38,
from about 336 mg to about 504 mg of the multiblock copolymer of Formula I,
from about 4.74 mg to about 37.9 mg of iron,
from about 450 to about 650 mg of trehalose,
from about 0.0005 mg to about 0.2 mg of 10-hydroxy camptothecin,
and from about 0.0005 mg to about 0.2 mg of 10-hydroxy-7-methyl camptothecin.

In some embodiments, the present invention provides methods for treating, stabilizing, or lessening the severity or progression of one or more proliferation diseases (e.g. cancer), wherein the method comprises administering to a patient in need thereof a pharmaceutically acceptable composition comprising
from about 14.4 mg to about 17.6 mg of SN-38,
from about 336 mg to about 504 mg of the multiblock copolymer of Formula I,
from about 4.74 mg to about 37.9 mg of iron,
from about 450 to about 650 mg of trehalose,
from about 0.001 mg to about 0.4 mg of 7-ethyl camptothecin,
from about 0.0005 mg to about 0.2 mg of 10-hydroxy camptothecin,
and from about 0.0005 mg to about 0.2 mg of 10-hydroxy-7-methyl camptothecin.

In some embodiments, the present invention provides methods for treating, stabilizing, or lessening the severity or progression of one or more proliferation diseases (e.g. cancer), wherein the method comprises administering to a patient in need thereof a pharmaceutically acceptable composition comprising
about 16 mg of SN-38,
about 420 mg of the multiblock copolymer of Formula I, and about 12 mg of iron.

In some embodiments, the present invention provides methods for treating, stabilizing, or lessening the severity or progression of one or more proliferation diseases (e.g. cancer), wherein the method comprises administering to a patient in need thereof a pharmaceutically acceptable composition comprising
about 16 mg of SN-38,
about 420 mg of the multiblock copolymer of Formula I,
about 12 mg of iron,
and about 500 mg of trehalose.

In some embodiments, provided methods comprise the administrating to a patient in need thereof a pharmaceutically acceptable composition comprising SN-38, a multiblock copolymer of Formula I, and iron, one, two, three, or four times a day.

In some embodiments, provided methods comprise the administrating to a patient in need thereof a pharmaceutically acceptable composition comprising SN-38, a multiblock copolymer of Formula I, iron, and trehalose one, two, three, or four times a day.

In some embodiments, provided methods comprise administering a pharmaceutically acceptable composition comprising SN-38, multiblock copolymer of Formula I, and iron once a day ("QD").

In some embodiments, provided methods comprise administering a pharmaceutically acceptable composition comprising SN-38, a multiblock copolymer of Formula I, and iron, or a pharmaceutically acceptable salt thereof, twice a day. In some embodiments, a pharmaceutically acceptable composition comprising SN-38, a multiblock copolymer of Formula I, and iron is administered once or twice daily for a period of 1, 2, 3, 4, 5, 6, 7, 8, 9, 10, 11, 12, 13, 14, 15, 16, 17, 18, 19, 20, 21, 22, 23, 24, 25, 26, 27 or 28 days. In some embodiments, a pharmaceutically acceptable composition comprising SN-38, a multiblock copolymer of Formula I, and iron is administered once daily for a period of 1, 2, 3, 4, 5, 6, 7, 8, 9, 10, 11, 12, 13, 14, 15, 16, 17, 18, 19, 20, 21, 22, 23, 24, 25, 26, 27 or 28 days.

In some embodiments, a pharmaceutically acceptable composition comprising SN-38, a multiblock copolymer of Formula I, and iron is administered once or twice daily for an amount of time during a period of 28 days ("a 28-day cycle"). In some embodiments, a pharmaceutically acceptable composition comprising SN-38, a multiblock copolymer of Formula I, and iron, is administered once or twice daily for at least one 28-day cycle. In some embodiments, a pharmaceutically acceptable composition comprising SN-38, a multiblock copolymer of Formula I, and iron, is administered once daily for 21 consecutive days of at least one 28-day cycle. In some embodiments, a pharmaceutically acceptable composition comprising SN-38, a multiblock copolymer of Formula I, and iron, or a pharmaceutically acceptable salt thereof, is administered once or twice daily for at least two, at least three, at least four, at least five or at least six 28-day cycles. In some embodiments, a pharmaceutically acceptable composition comprising SN-38, a multiblock copolymer of Formula I, and iron, or a pharmaceutically acceptable salt thereof, is administered once or twice daily for at least seven, at least eight, at least nine, at least ten, at least eleven or at least twelve 28-day cycles. In some embodiments, a pharmaceutically acceptable composition comprising SN-38, a multiblock copolymer of Formula I, and iron, or a pharmaceutically acceptable salt thereof, is administered once or twice daily for at least thirteen, at least fourteen, at least fifteen, at least sixteen, at least seventeen, at least eighteen, at least nineteen or at least twenty 28-day cycles. In some embodiments, a pharmaceutically acceptable composition comprising SN-38, a multiblock copolymer of Formula I, and iron, is administered to a patient for the duration of the patient's life.

In some embodiments, two adjacent 28-day cycles may be separated by a rest period. Such a rest period may be one, two, three, four, five, six, seven or more days during which the patient is not administered a composition comprising SN-38, a multiblock copolymer of Formula I, and iron.

In some embodiments, a pharmaceutically acceptable composition comprising SN-38, a multiblock copolymer of Formula I, and iron is administered once or twice daily for an amount of time during a period of 21 days ("a 21-day cycle"). In some embodiments, a pharmaceutically acceptable composition comprising SN-38, a multiblock copolymer of Formula I, and iron, is administered once or twice daily for at least one 21-day cycle. In some embodiments, a pharmaceutically acceptable composition comprising SN-38, a multiblock copolymer of Formula I, and iron, is administered once daily for 21 consecutive days of at least one 21-day cycle. In some embodiments, a pharmaceutically acceptable composition comprising SN-38, a multiblock copolymer of Formula I, and iron, or a pharmaceutically acceptable salt thereof, is administered once or twice daily for at least two, at least three, at least four, at least five or at least six 21-day cycles. In some embodiments, a pharmaceutically acceptable composition comprising SN-38, a multiblock copolymer of Formula I, and iron, or a pharmaceutically acceptable salt thereof, is administered once or twice daily for at least seven, at least eight, at least nine, at least ten, at least eleven or at least twelve 21-day cycles. In some embodiments, a pharmaceutically acceptable composition comprising SN-38, a multiblock copolymer of Formula I, and iron, or a pharmaceutically acceptable salt thereof, is administered once or twice daily for at least thirteen, at least fourteen, at least fifteen, at least sixteen, at least seventeen, at least eighteen, at least nineteen or at least twenty 21-day cycles. In some embodiments, a pharmaceutically acceptable composition comprising SN-38, a multiblock copolymer of Formula I, and iron, is administered to a patient for the duration of the patient's life.

In some embodiments, two adjacent 21-day cycles may be separated by a rest period. Such a rest period may be one, two, three, four, five, six, seven or more days during which the patient is not administered a composition comprising SN-38, a multiblock copolymer of Formula I, and iron.

In a preferred embodiment, a pharmaceutically acceptable composition comprising SN-38, multiblock copolymer of Formula I, and iron is administered once a week.

In a preferred embodiment, a pharmaceutically acceptable composition comprising SN-38, multiblock copolymer of Formula I, and iron is administered once a week for 3 weeks of a 28-day cycle.

In a preferred embodiment, a pharmaceutically acceptable composition comprising SN-38, multiblock copolymer of Formula I, and iron is administered on days 1 and 15 of a 28-day cycle.

In a preferred embodiment, a pharmaceutically acceptable composition comprising SN-38, multiblock copolymer of Formula I, and iron is administered on days 1, 8, and 15 of a 28-day cycle.

In a preferred embodiment, a pharmaceutically acceptable composition comprising SN-38, multiblock copolymer of Formula I, and iron is administered on day 1 of 28-day cycle.

In a preferred embodiment, a pharmaceutically acceptable composition comprising SN-38, multiblock copolymer of Formula I, and iron is administered on day 1 of 21-day cycle.

3.4 Administration

Some embodiments of the present invention provide methods for preparing a solution for administration to a patient. The general method for proving said solution comprises reconstituting each vial of a composition comprising SN-38, multiblock copolymer of Formula I, and iron with 20 mL of COLD (2-8° C.) NS or D5W to avoid the effects of thermal gelation. Thermal gelation is a reversible temperature and concentration dependent process that applies to colloidal formulations. As such, thermal gelation can occur during the reconstitution of lyophilized micelle formulations. The use of warm diluent for reconstitution results in a mixture of nanometer-sized micelles in solution and micron sized, partially un-reconstituted micelle gels. The use of cold saline prevents thermal gelation and the formation of gels.

Some embodiments of the present invention provide methods for preparing a solution for administration to a patient. The general method for proving said solution comprises the steps of removing a vial of a composition comprising SN-38, multiblock copolymer of Formula I, and iron vial from refrigerated storage, removing the plastic cap, adding 20 ml of COLD (2-8° C.) NS or D5W to the vial, inverting the vial by hand (do not shake) 2-3 times per second for 60 seconds (final vial concentration will be 0.8 mg/mL of SN-38 (no powder displacement should occur)), withdraw calculated dose from vial(s) and add to 250 mL of NS or D5W (please note that at higher dose levels where drug volume may exceed 100 mL, the site must ensure that the IV bag can accommodate 250 mL of NS or D5W in addition to drug volume (this solution does not need to be cold)), administer intravenously over one hour using 1.2 micron inline filter, discard any unused portion in the vial(s) (the final infusion volume will be variable depending upon the number of vials reconstituted for the dose, the maximum infusion volume may not exceed 500 mL).

In some embodiments, the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, and iron wherein the administration is parenteral. In a preferred embodiment the administration is intravenous. In another preferred embodiment the administration is via a central venous catheter.

In some embodiments, the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, and iron wherein the administration is performed over about 30 to about 90 minutes. In a preferred embodiment the administration is performed over about 60 minutes.

In some embodiments, the present invention provides methods for treating, stabilizing, or lessening the severity or progression of one or more proliferation diseases (e.g. cancer, as described herein), wherein the method comprises administering to a patient in need thereof a pharmaceutically acceptable composition comprising SN-38, multiblock copolymer of Formula I, and iron wherein the dose of SN-38 is about 1 to about 30 mg/m$^2$ body surface area. In other embodiments, the dose of SN-38 is about 1 to about 4 mg/m$^2$ body surface area. In other embodiments, the dose of SN-38 is about 4 to about 8 mg/m$^2$ body surface area. In other embodiments, the dose of SN-38 is about 8 to about 12 mg/m$^2$ body surface area. In other embodiments, the dose of SN-38 is about 12 to about 16 mg/m$^2$ body surface area. In other embodiments, the dose of SN-38 is about 16 to about 20 mg/m$^2$ body surface area.

In some embodiments, the present invention provides methods for treating, stabilizing, or lessening the severity or progression of one or more proliferation diseases (e.g. cancer, as described herein), wherein the method comprises administering to a patient in need thereof a pharmaceutically acceptable composition comprising SN-38, multiblock copolymer of Formula I, and iron wherein the dose of SN-38 is about 3 mg/m$^2$ body surface area. In other embodiments, the dose of SN-38 is about 4 mg/m$^2$ body surface area. In other embodiments, the dose of SN-38 is about 6 mg/m$^2$ body surface area. In other embodiments, the dose of SN-38 is about 8 mg/m$^2$ body surface area. In other embodiments, the dose of SN-38 is about 10 mg/m$^2$ body surface area. In other embodiments, the dose of SN-38 is about 12 mg/m$^2$ body surface area. In other embodiments, the dose of SN-38 is about 16 mg/m$^2$ body surface area. In other embodiments, the dose of SN-38 is about 20 mg/m$^2$ body surface area.

In some embodiments, the present invention provides methods for treating, stabilizing, or lessening the severity or progression of one or more proliferation diseases (e.g. cancer, as described herein), wherein the method comprises administering to a patient in need thereof a pharmaceutically acceptable composition comprising SN-38, multiblock copolymer of Formula I, and iron wherein the dose of SN-38 is about 4 to about 12 mg/m² body surface area.

In some embodiments, the present invention provides methods for treating, stabilizing, or lessening the severity or progression of one or more proliferation diseases (e.g. cancer), wherein the method comprises administering to a patient in need thereof a pharmaceutically acceptable composition comprising SN-38, multiblock copolymer of Formula I, and iron wherein the dose of SN-38 is about 1 to about 80 mg SN-38. In other embodiments, the dose of SN-38 is about 5 to about 30 mg SN-38. In other embodiments, the dose of SN-38 is about 10 to about 40 mg SN-38.

In some embodiments, the present invention provides methods for treating, stabilizing, or lessening the severity or progression of one or more proliferation diseases (e.g. cancer, as described herein), wherein the method comprises administering to a patient in need thereof a pharmaceutically acceptable composition comprising SN-38, multiblock copolymer of Formula I, and iron wherein the dose of SN-38 is about 4 to about 24 mg SN-38.

In some embodiments, the present invention provides methods for treating, stabilizing, or lessening the severity or progression of one or more proliferation diseases (e.g. cancer, as described herein), wherein the method comprises administering to a patient in need thereof a pharmaceutically acceptable composition comprising SN-38, multiblock copolymer of Formula I, and iron wherein the resulting plasma concentration of SN-38 is about 10 to about 2,500 ng/mL SN-38. In other embodiments, the plasma concentration of SN-38 is about 50 to about 500 ng/mL SN-38. In other embodiments, the plasma concentration of SN-38 is about 100 to about 1,000 ng/mL SN-38. In other embodiments, the plasma concentration of SN-38 is about 80 to about 400 ng/mL SN-38. In other embodiments, the plasma concentration of SN-38 is about 150 to about 1,500 ng/mL SN-38.

In some embodiments, the present invention provides methods for treating, stabilizing, or lessening the severity or progression of one or more proliferation diseases (e.g. cancer, as described herein), wherein the method comprises administering to a patient in need thereof a pharmaceutically acceptable composition comprising SN-38, multiblock copolymer of Formula I, and iron wherein the resulting plasma exposure of SN-38 is about 100 to about 10,000 ng*h/mL SN-38. In other embodiments, the plasma concentration of SN-38 is about 100 to about 1,000 ng*h/mL SN-38. In other embodiments, the plasma concentration of SN-38 is about 200 to about 2,000 ng/mL SN-38. In other embodiments, the plasma concentration of SN-38 is about 400 to about 4,000 ng*h/mL SN-38. In other embodiments, the plasma concentration of SN-38 is about 500 to about 5,000 ng*h/mL SN-38. In other embodiments, the plasma concentration of SN-38 is about 1,000 to about 10,000 ng*h/mL SN-38. In other embodiments, the plasma concentration of SN-38 is about 50 to about 2,000 ng*h/mL SN-38.

Without wishing to be bound to any particular theory, it is believed that administration of IT-141, as described above and herein, results in improved anti-tumor efficacy as compared to irinotecan. Pharmacokinetic parameters of irinotecan and SN-38, resulting from administration of irinotecan to a patient in need thereof, are described in the FDA-approved package insert labeling information. Specifically, the FDA-approved prescribing information of irinotecan describes pharmacokinetics resulting from two dosages of irinotecan: 125 mg/m² and 340 mg/m². The reported maximum concentration ("$C_{max}$") of SN-38 resulting from administration of 125 mg/m² of irinotecan is 26 ng/mL. The $C_{max}$ of SN-38 resulting from administration of 340 mg/m² of irinotecan is 56 ng/mL. Surprisingly, the $C_{max}$ of SN-38 resulting from administration of 4 mg/m² of IT-141 is about 245 ng/mL. One of ordinary skill in the art will appreciate that the $C_{max}$ of SN-38 resulting from administration of IT-141 at a dose of 4 mg/m² to a patient in need thereof is more than about 9 times higher than the $C_{max}$ of SN-38 resulting from administration of irinotecan at a dose of 125 mg/m² that is more than 30 times higher to a patient in need thereof (i.e., a lower dose of IT-141 results in a higher $C_{max}$ as compared with a higher dose of irinotecan). One of ordinary skill in the art will also appreciate that the $C_{max}$ of SN-38 resulting from administration of IT-141 at a dose of 4 mg/m² to a patient in need thereof is more than about 4 times higher than the $C_{max}$ of SN-38 resulting from administration of irinotecan at a dose of 340 mg/m² that is 85 times higher to a patient in need thereof.

The FDA approved prescribing information of irinotecan further reports the plasma exposure ("AUC") of SN-38 resulting from administration of 125 mg/m² of irinotecan is 229 ng*h/mL. The AUC of SN-38 resulting from administration of 340 mg/m² of irinotecan is 474 ng*h/mL. It was surprisingly found that the AUC of SN-38 resulting from the administration of IT-141 at a dose of 4 mg/m² to a patient in need thereof is about 873 ng*h/mL. One of ordinary skill in the art will appreciate that the AUC of SN-38 resulting from administration of IT-141 at a dose of 4 mg/m² to a patient in need thereof is more than about 3 times higher than the AUC of SN-38 resulting from administration of irinotecan at a dose of 125 mg/m² that is more than 30 times higher to a patient in need thereof (i.e., a lower dose of IT-141 results in a higher AUC as compared with a higher dose of irinotecan). One of ordinary skill in the art will also appreciate that the AUC of SN-38 resulting from administration of IT-141 at a dose of 4 mg/m² to a patient in need thereof is about 1.8 times higher than the AUC of SN-38 resulting from administration of irinotecan at a dose of 340 mg/m² that is 85 times higher to a patient in need thereof.

It has been surprisingly found that administration of IT-141 to a patient, as described herein, results in:
(a) a maximum concentration of SN-38 that is about three times higher as compared to administration of a dose of irinotecan that is about 30 times higher than the dose of IT-141; and
(b) a plasma exposure of SN-38 that is higher as compared to administration of a dose of irinotecan that is about 30 times higher than the dose of IT-141.

Thus, in certain embodiments, the present invention provides a method of treating, stabilizing, or lessening the severity or progression of one or more proliferation diseases (e.g. cancer, as described herein), wherein the method comprises administering to a patient in need thereof a pharmaceutically acceptable composition comprising SN-38, multiblock copolymer of Formula I, and iron wherein the resulting plasma concentration of SN-38 is higher as compared to administration of irinotecan.

Without wishing to be bound to any particular theory, it is believed that administration of IT-141, as described above and herein, results in improved anti-tumor efficacy as compared to Onyvide® (irinotecan liposome injection). Pharmacokinetic parameters of SN-38 resulting from administration of Onyvide® to a patient in need thereof, are described in the FDA-approved package insert labeling information. Specifically, the FDA-approved prescribing information of Onyvide® states describes pharmacokinetics resulting from a dosage of Onyvide® of 70 mg/m². The reported $C_{max}$ of SN-38 resulting from administration of 70 mg/m² of Onyvide® is 5 ng/mL. Surprisingly, the $C_{max}$ of SN-38 resulting from administration of 4 mg/m² of IT-141 is about 245 ng/mL. One of ordinary skill in the art will appreciate that the $C_{max}$ of SN-38 resulting from administration of IT-141 at a dose of 4 mg/m² to a patient in need thereof is about 49 times higher than the $C_{max}$ of SN-38 resulting from administration of Onyvide® at a dose of 70 mg/m² that is more than 17 times higher to a patient in need thereof (i.e., a lower dose of IT-141 results in a higher $C_{max}$ as compared with a higher dose of Onyvide®).

The FDA approved prescribing information of Onyvide® further reports the AUC of SN-38 resulting from administration of 70 mg/m² of Onyvide® is 620 ng*h/mL. It was surprisingly found that the AUC of SN-38 resulting from the administration of IT-141 at a dose of 4 mg/m² to a patient in need thereof is about 873 ng*h/mL. One of ordinary skill in the art will appreciate that the AUC of SN-38 resulting from administration of IT-141 at a dose of 4 mg/m² to a patient in need thereof is about 1.4 times higher than the AUC of SN-38 resulting from administration of Onyvide® at a dose of 70 mg/m² that is more than 17 times higher to a patient in need thereof (i.e., a lower dose of IT-141 results in a higher AUC as compared with a higher dose of Onyvide®).

It has been surprisingly found that administration of IT-141 to a patient, as described herein, results in:
(c) a maximum concentration of SN-38 that is about 1.4 times higher as compared to administration of a dose of Onyvide® that is about 17 times higher than the dose of IT-141; and
(d) a plasma exposure of SN-38 that is higher as compared to administration of a dose of Onyvide® that is about 17 times higher than the dose of IT-141.

Thus, in certain embodiments, the present invention provides a method of treating, stabilizing, or lessening the severity or progression of one or more proliferation diseases (e.g. cancer, as described herein), wherein the method comprises administering to a patient in need thereof a pharmaceutically acceptable composition comprising SN-38, multiblock copolymer of Formula I, and iron wherein the resulting plasma concentration of SN-38 is higher as compared to administration of Onyvide®.

3.5 Unit Dosage Forms

In some embodiments, the present invention provides a unit dosage form comprising a formulation or composition described herein. The expression "unit dosage form" as used herein refers to a physically discrete unit of a provided formulation appropriate for the subject to be treated. It will be understood, however, that the total daily usage of provided formulation will be decided by the attending physician within the scope of sound medical judgment. The specific effective dose level for any particular subject or organism will depend upon a variety of factors including the disorder being treated and the severity of the disorder; activity of specific active agent employed; specific formulation employed; age, body weight, general health, sex and diet of the subject; time of administration, and rate of excretion of the specific active agent employed; duration of the treatment; drugs and/or additional therapies used in combination or coincidental with specific compound(s) employed, and like factors well known in the medical arts.

Compositions of the present invention can be provided as a unit dosage form. In some embodiments, a vial comprising of SN-38, multiblock copolymer of Formula I, iron, and trehalose is a unit dosage form.

Still further encompassed by the invention are pharmaceutical packs and/or kits comprising compositions described herein, or a unit dosage form comprising a provided composition, and a container (e.g., a foil or plastic package, or other suitable container). Optionally instructions for use are additionally provided in such kits.

TABLE 1

Pharmaceutical Components

| Component | Function | Weight % | Amount/vial |
|---|---|---|---|
| SN-38 | Active | 1.60 | 16 mg |
| Multiblock Copolymer of Formula I | Micelle forming polymer | 42.0 | 420 mg |
| Iron | Stabilizing agent | 1.20 | 12 mg |
| Trehalose | Cryoprotectant | 50.0 | 500 mg |

In some embodiments, the pharmaceutical composition is selected from those in Table 2:

TABLE 2

Pharmaceutical Components Ranges

| Component | Function | Weight % Range | Amount/vial |
|---|---|---|---|
| SN-38 | Active | 1.44-1.76 | 14.4-17.6 mg |
| Multiblock Copolymer of Formula I | Micelle forming polymer | 33.6-50.4 | 336-504 mg |
| Iron | Stabilizing agent | 0.5-4 | 5-40 mg |
| Trehalose | cryoprotectant | 45-65 | 450-650 mg |
| 7-Ethyl Camptothecin | Impurity | 0.0001-0.04 | 0.001-0.4 mg |

EXEMPLIFICATION

As described generally above, compositions comprising SN-38, a multiblock copolymer of Formula I, and iron, including drug loaded micelles, are described in U.S. patent application Ser. No. 13/840,133, filed Mar. 15, 2013, published as US 2013-0280306 A1 on Oct. 24, 2013, the entirety of which is hereby incorporated by reference. Multiblock copolymer of Formula I is described in U.S. Pat. No. 9,078,930 (published on Oct. 24, 2013 as U.S. patent application serial number 2013/0280306 A1), and in U.S. patent application Ser. No. 14/028,485 (referred herein as the "the 485 application"; published May 8, 2014 as US 2014-0127271) the entirety of which is hereby incorporated herein by reference.

As depicted in the Examples below, in certain exemplary embodiments, methods are performed according to the general procedures. It will be appreciated that, although the general methods depict certain methods of the present invention, the following general methods, and others known to one of ordinary skill in the art, can be applied to all methods described herein.

Thermal Gelation

Reconstitution of a formulation comprising SN-38, multiblock copolymer of Formula I, iron, and trehalose in saline is dependent on temperature. FIG. 5 shows optical micrographs of solutions of a formulation comprising SN-38, multiblock copolymer of Formula I, iron, and trehalose reconstituted with 4° C. and 40° C. saline before and after filtration through a 1.2 μm filter. At 4° C., no micro-sized gels are present. At 40° C., gel aggregates are present which can be removed by filtration.

Without wishing to be bound to any particular theory, the effect of saline temperature on reconstitution is believed to be a phenomenon referred to as thermal gelation in the literature as follows. Thermal gelation is a reversible temperature and concentration dependent process that applies to colloidal formulations (Bowman, B. J., Ofner, C. M. and Schott, H., 2005. Colloidal dispersions. *Remington: The Science and Practice of Pharmacy*, 21st ed., Lippincott-Williams, New York, pp. 293-318). As such, thermal gelation can occur during the reconstitution of lyophilized micelle formulations such as the present invention. The reconstitution conditions for a formulation comprising SN-38, multiblock copolymer of Formula I, iron, and trehalose require the use of cold (2-8° C.) saline to avoid thermal gelation.

The present invention includes a lyophilized powder comprising SN-38, multiblock copolymer of Formula I, iron, imbedded in a trehalose matrix. This powder possesses waters of hydration (i.e. water molecules associated with the micelles that can be removed or displaced through heating without changing the chemical composition of the micelles) that allow the powder to be "wetted" by diluent (either saline or 5% dextrose injection) upon reconstitution. The diluent can fully permeate the powder when the waters of hydration are present, at the appropriate temperatures, allowing the powder to rapidly disperse into a uniform solution of nanometer-sized micelles. At temperatures above ca. 20° C. the lyophilized powder loses the waters of hydration, (i.e. the water molecules are no longer closely bound to the powder) which prevents the diluent from rapidly and efficiently wetting the powder upon reconstitution. The result is an incomplete wetting and dispersion of the powder that causes the formation of micron sized gelatinous aggregates of unreconstituted micelles. These gel aggregates of partially unreconstituted micelles can be observed in solution as 5 to 50 □m particles. The gel aggregates will eventually reconstitute as wetting occurs throughout the gel causing it to completely disperse into nanometer-sized micelles. Once the nanometer micelles are in solution they cannot aggregate or revert to gels even at higher temperature because thermal gelation cannot occur after complete wetting or hydration (i.e., hydration is not reversible).

FIG. 6 shows the effect of saline temperature on solution turbidity 1 minute following reconstitution of lyophilized powder comprising SN-38, multiblock copolymer of Formula I, and trehalose at 5 mg/mL. Above 20° C., turbidity increases due to onset of thermal gelation causing incomplete wetting and dispersion of the powder and the associated formation of partially reconstituted micron sized gel aggregates. The use of warm (c.a. 40° C.) saline for reconstitution results in a mixture of nanometer-sized micelles in solution and micron sized, partially unreconstituted micelle gels.

Table 3 shows the results of reconstitution of a formulation comprising SN-38, multiblock copolymer of Formula I, iron, and trehalose at 1 and 50 mg/mL using 4° C. and 40° C. saline (the concentration range of 1 to 50 mg/mL covers solutions made for clinical use, similar results are obtained at concentrations as high as 150 mg/mL, which covers stock solutions used for some nonclinical safety studies). One minute after reconstitution at 4° C., complete reconstitution into nanometer sized micelles is observed, while at 40° C., sixty percent reconstitutes into nanometer sized micelles, with the forty percent forming micron sized gel aggregates. Heating the reconstituted solutions for 24 hours at 40° C. does not affect existing micelles while the gels slowly become wetted and disperse into micelles.

TABLE 3

Micelle properties of a formulation comprising SN-38, multiblock copolymer of Formula I, iron, and trehalose reconstituted at 1 and 50 mg/mL using 4° C. and 40° C. saline.

| Formulation comprising SN-38, multiblock copolymer of Formula I, iron, and trehalose concentration (mg/mL) | Saline Temperature (° C.) | Percent Micelle (% w/w) | Micelle Particle Size (nm) |
|---|---|---|---|
| 1 Minute After Reconstitution ||||
| 1 | 4 | 97 | 67 |
| 50 | 4 | 100 | 60 |
| 1 | 40 | 61 | 58 |
| 50 | 40 | 50 | 58 |
| After Stirring for 24 Hours ||||
| 1 | 4 | 98 | 61 |
| 50 | 4 | 98 | 50 |
| 1 | 40 | 66 | 61 |
| 50 | 40 | 65 | 70 |

Batch Analysis of Drug Product

Batch analysis data for two lots of a composition comprising SN-38, a multiblock copolymer of Formula I, iron, and trehalose is reproduced in Table 4.

TABLE 4

Batch analysis data for drug product comprising SN-38, a multiblock copolymer of Formula I, iron, and trehalose lots 848-28 and 848-34

| | | Results ||
|---|---|---|---|
| Test | Acceptance Criteria | Lot 848-28 | Lot 848-34 |
| Appearance | Tan to brown cake | Tan to brown cake | Tan to brown cake |
| Appearance (reconstituted) | Tan to brown solution, free of visual particulates | Tan to brown, no particulates | Tan to brown, no particulates |
| Identification SN-38 | Retention time of sample comparable to standard | Conforms | Conforms |
| Identification Multiblock Copolymer of Formula I | Retention time of sample comparable to standard | Conforms | Conforms |
| Assay SN-38 (%) | 90.0 to 110.0% of LC | 97.5 | 83.1 |
| Assay Multiblock | 80.0 to 120.0% of LC | 109.0 | 81.7 |

TABLE 4-continued

Batch analysis data for drug product comprising SN-38, a multiblock copolymer of Formula I, iron, and trehalose lots 848-28 and 848-34

| | | Results | |
|---|---|---|---|
| Test | Acceptance Criteria | Lot 848-28 | Lot 848-34 |
| Copolymer of Formula I (%) | | | |
| Related substances SN-38 (%) | NMT 2% | 0.3 | 0.3 |
| 7-ethyl camptothecin Individual unspecified | NMT 1.0% | | |
| RRT 0.56 | | 0.2 | 0.2 |
| RRT 0.66 | | 0.1 | 0.1 |
| RRT 0.75 | | 0.1 | 0.1 |
| RRT 0.88 | | 0.4 | 0.7 |
| Total | NMT 5% | 1.2 | 1.5 |
| Related substances multiblock copolymer of formula I (%) Individual unspecified RRT 2.1 | Report each | ND | 0.7 |
| Uniformity of dosage units | Complies with USP<905> | NT | AV 19 |
| Residual DMSO (ppm) | NMT 5,000 ppm | 2,260 | 4,735 |
| Water content (%) | NMT 10% | 3 | 2 |
| pH | 5.0 to 7.0 | 5.7 | 6.1 |
| Particle size (reconstituted) $D_{50}$ (nm) | 20 to 140 nm | 65.2 | 67.2 |
| Iron content (%) | 0.5 to 4% LC | 1.3 | 1.0 |
| Particulate matter | Complies with USP<789> | NT | NT |
| Bacterial endotoxins | NMT 50 EU/vial | NT | NT |
| Sterility | Sterile | NT | NT |

DMSO = dimethyl sulfoxide;
LC = label claim;
NMT = not more than;
ND = not detected;
NT = not tested;
USP = United States Pharmacopeia;
RRT = relative retention time Stability Data Stability data for a composition comprising SN-38, a multiblock copolymer of Formula I, iron, and trehalose for lot 848-34 is reproduced in Table 5 and Table 6.

TABLE 5

Long-term (2 to 8° C.) stability and reconstitution data for drug product comprising SN-38, a multiblock copolymer of Formula I, iron, and trehalose lot 848-34

| | Stability Interval (Months) | | |
|---|---|---|---|
| Test | Initial | 3 | 6 |
| Appearance | Tan to brown cake | Tan to brown cake | Tan to brown cake |
| Appearance (reconstituted) | Tan to brown solution, free of visual particulates | Tan to brown solution, free of visual particulates | Tan to brown solution, free of visual particulates |
| Reconstitution time | 8 min 10 sec | 8 min 3 sec | 8 min 22 sec |
| Assay SN-38 (%) | 83.1 | 97.5 | 103.8 |
| Assay multiblock copolymer of Formula I (%) | 81.7 | 73.1 | 90.0 |
| SN-38 related substances (%) | 0.3 | NT | NT |
| 7-ethyl camptothecin Individual unspecified | | | |
| RRT 0.56 | 0.2 | | |
| RRT 0.66 | 0.1 | | |
| RRT 0.75 | 0.1 | | |
| RRT 0.88 | 0.7 | | |
| Total | 1.5 | | |
| multiblock copolymer of Formula I related substances (%) | 0.7 | 4.21 | 0.63 |

TABLE 5-continued

Long-term (2 to 8° C.) stability and reconstitution data for drug product comprising SN-38, a multiblock copolymer of Formula I, iron, and trehalose lot 848-34

| | Stability Interval (Months) | | |
|---|---|---|---|
| Test | Initial | 3 | 6 |
| RRT 2.1 | | | |
| Water content (%) | 2.0 | 1.39 | 1.34 |
| pH | 6.1 | 6.3 | 6.1 |
| Particle size (nm) | 67.2 | 76.4 | 64.3 |

NT = not tested;
RRT = relative retention time

TABLE 6

Long-term (2 to 8° C.) stability data for drug product comprising SN-38, a multiblock copolymer of Formula I, iron, and trehalose Lot 848-34

| | Stability Interval (months) | | | | | | | | | |
|---|---|---|---|---|---|---|---|---|---|---|
| Test | Initial | 0.25 | 0.5 | 1 | 2 | 3 | 6 | 9 | 12 | 24 |
| Appearance | Tan/orange powder | Tan/orange powder | Tan/orange powder | Tan/orange powder | Tan/orange powder | Tan/orange powder | Tan/orange powder | Tan/orange powder | Tan/orange powder | Tan/orange powder |
| Appearance (reconstituted) | Orange clear liquid | Orange clear liquid | Orange clear liquid | Orange clear liquid | Orange clear liquid | Orange clear liquid | Orange clear liquid | Orange clear liquid | Orange clear liquid | Orange clear liquid |
| Assay SN-38 (mg/vial) | 10.6 | 10.8 | 12.5 | 12.8 | 12.4 | 12.6 | 12.1 | 12.0 | 11.9 | 12.2 |
| Assay multiblock copolymer of Formula I (mg/vial) | 289 | 355 | 371 | 331 | 354 | 300 | 324 | 339 | 340 | 343 |
| pH | 7.1 | 6.0 | 5.7 | 6.8 | 6.7 | 6.9 | 6.5 | 7.0 | 6.8 | 7.0 |
| Particle size (nm) | 55.6 | 56.1 | 59.7 | 55.1 | 70 | 77.83 | 65.9 | 54.3 | 54.6 | 62.8 |

NT = not tested

Stability data for a composition comprising SN-38, a multiblock copolymer of Formula I, iron, and trehalose for lot 848-28 is reproduced in Table 7. These data demonstrate no change in physiochemical properties over a 2 year period.

Clinical Trial Data

Data was collected during a phase 1 clinical trial in the United States. Patients had advanced solid tumors. Investigational product (IT-141, Table 1, above) was dosed on days

TABLE 7

Long-term (2 to 8° C.) stability data for drug product comprising SN-38, a multiblock copolymer of Formula I, iron, and trehalose Lot 848-28

| | Stability Interval (months) | | | | | | | | | |
|---|---|---|---|---|---|---|---|---|---|---|
| Test | Initial | 0.25 | 0.5 | 1 | 2 | 3 | 6 | 9 | 12 | 24 |
| Appearance | tan powder | tan powder | tan powder | tan powder | tan powder | tan powder | tan powder | tan powder | tan powder | tan powder |
| Appearance (reconstituted) | orange clear liquid | orange clear liquid | orange clear liquid | orange clear liquid | orange clear liquid | orange clear liquid | orange clear liquid | orange clear liquid | orange clear liquid | orange clear liquid |
| Assay SN-38 (mg/vial) | 16.7 | 16.1 | 16.7 | 15.6 | 17.2 | 17.9 | 17.1 | 15.8 | 15.4 | 15.9 |
| Assay multiblock copolymer of Formula I (mg/vial) | NT | NT | NT | NT | NT | NT | 518 | 461 | 437 | 502 |
| pH | 5.9 | 5.9 | 5.9 | 5.9 | 5.9 | 5.9 | 5.9 | 5.8 | 5.6 | 5.7 |
| Particle size (nm) | 73.3 | 50.3 | 62.3 | 45.8 | 70.1 | 76.7 | 82.2 | 60.9 | 85 | 67 |

NT = not tested 1 and 15 of a 28-day cycle. Dosing was performed with a 60-minute intravenous infusion. Plasma was collected 15 and 30 min, 1, 2, 4, 8, 12, 24, 48, 72, 96, and 168 hours after beginning the infusion. Each aliquot was assayed for SN-38 and SN-38G (SN-38 glucuronide) concentrations by LC-MS/MS.

Subject 004, a 55 year old female with colorectal cancer, was administered IT-141 at 1 mg/m². Subject 004 was UGT1A1*28 heterozygous. Subject 004 had a BSA of 1.7, so 1.7 mg of SN-38 was administered. Plasma was collected on cycle 1, day 1 according to the schedule above. The pharmacokinetic data is plotted in FIG. 7. The $C_{max}$ for SN-38 was 59.9 ng/mL. The AUC of SN-38 was 137.9 h*ng/mL. The half life of SN-38 was 6.4 h. The $C_{max}$ for SN-38G was 22.7 ng/mL. The AUC of SN-38G was 123.9 h*ng/mL. The half life of SN-38G was 10.0 h. Subject 004 had stable disease by RECIST criteria after the first cycle, and completed 3 cycles (7 doses of IT-141). Subject 004 reported grade 2 diarrhea through cycles 1 and 2, and grade 3 diarrhea in cycle 3.

Subject 006, a 62 year old female with lung cancer, was administered IT-141 at 2 mg/m². Subject 006 was UGT1A1*28 wild type. Subject 006 had a BSA of 1.8, so 3.6 mg of SN-38 was administered. Plasma was collected on cycle 1, day 1 and cycle 2, day 1according to the schedule above. The pharmacokinetic data is plotted in FIG. 8 and FIG. 9. For the first cycle, the $C_{max}$ for SN-38 was 55.8 ng/mL. The AUC of SN-38 was 140.0 h*ng/mL. The half life of SN-38 was 3.1 h. The $C_{max}$ for SN-38G was 82.1 ng/mL. The AUC of SN-38G was 280.5 h*ng/mL. The half life of SN-38G was 1.5 h. For the second cycle, the $C_{max}$ for SN-38 was 50.6 ng/mL. The AUC of SN-38 was 137.0 h*ng/mL. The half life of SN-38 was 4.7 h. The $C_{max}$ for SN-38G was 76.7 ng/mL. The AUC of SN-38G was 221.0 h*ng/mL. Subject 006 had stable disease by RECIST criteria after the first cycle, and completed 7 cycles (14 doses of IT-141) before being removed from the study for progressive disease. Subject 006 reported no adverse events.

Subject 007, a 52 year old male with colorectal cancer, was administered IT-141 at 1 mg/m². Subject 007 was UGT1A1*28 heterozygous. Subject 007 had a BSA of 2.1, so 2.1 mg of SN-38 was administered. Plasma was collected on cycle 1, day 1 and cycle 2, day 1according to the schedule above. The pharmacokinetic data is plotted in FIG. 10 and FIG. 11. For the first cycle, the $C_{max}$ for SN-38 was 31.4 ng/mL. The AUC of SN-38 was 89.5 h*ng/mL. The half life of SN-38 was 4.1 h. The $C_{max}$ for SN-38G was 44.0 ng/mL. The AUC of SN-38G was 208.7 h*ng/mL. For the second cycle, the $C_{max}$ for SN-38 was 21.3 ng/mL. The AUC of SN-38 was 94.2 h*ng/mL. The half life of SN-38 was 2.9 h. The $C_{max}$ for SN-38G was 40.6 ng/mL. The AUC of SN-38G was 263.4 h*ng/mL. Subject 007 completed 1 cycle (3 doses of IT-141) and was removed from the study due to a severe adverse event (not drug related). Subject 007 had a hypersensitivity reaction during the second infusion. Subject 007 reported no other adverse events. No tumor evaluation was made as the patient did not complete two cycles of treatment.

Subject 008, a 65 year old female with colon cancer, was administered IT-141 at 4 mg/m². Subject 008 was UGT1A1*28 wild type. Subject 008 had a BSA of 1.5, so 6 mg of SN-38 was administered. Plasma was collected on cycle 1, day 1 according to the schedule above. The pharmacokinetic data is plotted in FIG. 12. The $C_{max}$ for SN-38 was 245 ng/mL. The AUC of SN-38 was 873 h*ng/mL. The half life of SN-38 was 35.4 h. The $C_{max}$ for SN-38G was 345 ng/mL. The AUC of SN-38G was 5,103 h*ng/mL. The half life of SN-38G was 62.3 h. Subject 008 completed 1 dose of IT-141 and was removed from the study due to kidney failure (deemed not drug related). Subject 008 reported grade 2 diarrhea. No tumor evaluation was made as the patient did not complete two cycles of treatment.

We claim:

1. A composition comprising SN-38, iron, and multiblock copolymer of Formula I:

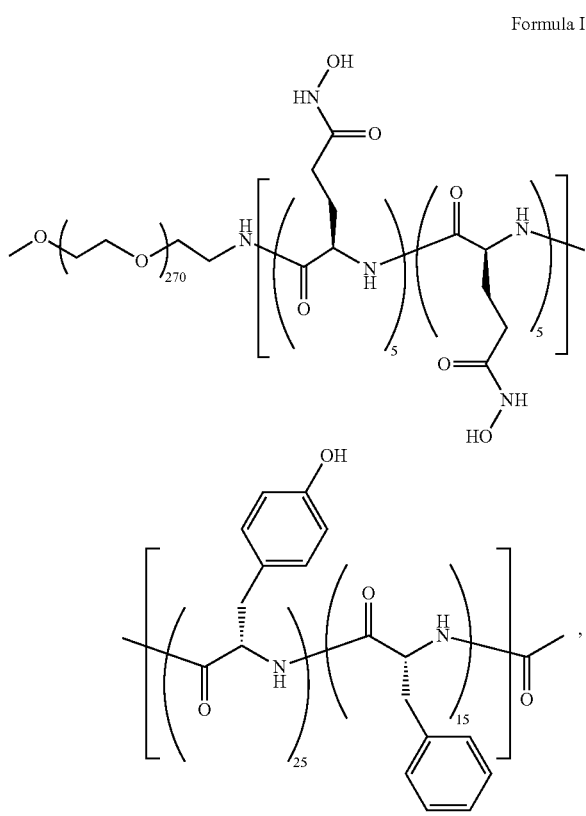

Formula I wherein:
the SN-38 is between about 0.5 and about 2.5 weight percentage of the composition;
the iron is between about 0.01 and about 5 weight percentage of the composition; and
the multiblock copolymer of Formula I is between about 20 and about 60 weight percentage of the composition.

2. The composition according to claim 1, wherein said composition further comprises a cryoprotectant.

3. The composition according to claim 2, wherein the cryoprotectant is trehalose.

4. The composition according to claim 2, further comprising at least one of 7-ethyl camptothecin, 10-hydroxy camptothecin, and 10-hydroxy-7-methyl camptothecin.

5. The composition according to claim 4, wherein the 7-ethyl camptothecin is between about 0.0001 and about 0.04 weight percent of the composition, the 10-hydroxy camptothecin is between about 0.00005 and about 0.02 weight percent of the composition, and the 10-hydroxy-7-methyl camptothecin is between about 0.00005 and about 0.02 weight percent of the composition.

6. The composition according to claim 1, wherein:
the SN-38 is between about 1.60 and about 1.77 weight percentage of the composition, the iron is between about 1.01 and about 1.52 weight percentage of the composition; and the multiblock copolymer of Formula I is between about 39.9 and about 48.7 weight percentage of the composition.

7. The composition according to claim 2, wherein:

the SN-38 is between about 0.5 and about 2.5 weight percentage of the composition;

the iron is between about 0.01 and about 5 weight percentage of the composition;

the multiblock copolymer of Formula I is between about 20 and about 60 weight percentage of the composition; and the cryoprotectant is between about 20 and about 80 weight percentage of the composition.

8. The composition according to claim 3, wherein:

the SN-38 is between about 0.5 and about 2.5 weight percentage of the composition;

the iron is between about 0.01 and about 5 weight percentage of the composition;

the multiblock copolymer of Formula I is between about 20 and about 60 weight percentage of the composition; and the trehalose is between about 20 and about 80 weight percentage of the composition.

9. A method for treating a cancer, in a patient in need thereof, comprising administering to the patient the composition according to claim 1.

10. The method according to claim 9, wherein the cancer is selected from pancreatic, lung, gastroesophageal, colorectal cancer, or gastrointestinal cancer, or breast.

11. The composition according to claim 6, wherein said composition further comprises a cryoprotectant.

12. The composition according to claim 11, wherein the cryoprotectant is trehalose.

13. The composition according to claim 11, further comprising at least one of 7-ethyl camptothecin, 10-hydroxy camptothecin, and 10-hydroxy-7-methyl camptothecin.

14. The composition according to claim 13, wherein the 7-ethyl camptothecin is between about 0.0001 and about 0.04 weight percent of the composition, the 10-hydroxy camptothecin is between about 0.00005 and about 0.02 weight percent of the composition, and the 10-hydroxy-7-methyl camptothecin is between about 0.00005 and about 0.02 weight percent of the composition.

15. The method according to claim 9, wherein administration at a dose of 4 mg/m$^2$ to a patient in need thereof achieves a $C_{max}$ of SN-38 of about 100 to about 1,000 ng/mL.

16. The method according to claim 9, wherein administration at a dose of 4 mg/m$^2$ to a patient in need thereof achieves an AUC of SN-38 of about 400 to about 4,000 ng*h/mL.

* * * * *